US010902351B1

(12) United States Patent
Neumann

(10) Patent No.: US 10,902,351 B1
(45) Date of Patent: Jan. 26, 2021

(54) METHODS AND SYSTEMS FOR USING ARTIFICIAL INTELLIGENCE TO ANALYZE USER ACTIVITY DATA

(71) Applicant: Kenneth Neumann, Lakewood, CO (US)

(72) Inventor: Kenneth Neumann, Lakewood, CO (US)

(73) Assignee: KPN INNOVATIONS, LLC, Lakewood, CO (US)

( * ) Notice: Subject to any disclaimer, the term of this patent is extended or adjusted under 35 U.S.C. 154(b) by 0 days.

(21) Appl. No.: 16/532,283

(22) Filed: Aug. 5, 2019

(51) Int. Cl.
*G06N 20/00* (2019.01)

(52) U.S. Cl.
CPC ................ *G06N 20/00* (2019.01)

(58) Field of Classification Search
CPC .......... G06N 20/00; G06F 17/30522; G06F 17/30525; G06F 17/30528; G06F 17/30554; G06F 17/30557; G06Q 30/01; G06Q 30/0615; G06K 9/00107; G06K 9/00087; G06K 9/00906; H04L 29/06; H04L 12/26; H04L 29/08; H04L 29/12
USPC ......................................................... 709/204
See application file for complete search history.

(56) References Cited

U.S. PATENT DOCUMENTS

| 6,317,722 B1 | 11/2001 | Jacobi et al. | |
| 7,542,924 B2 | 6/2009 | Chow et al. | |
| 9,607,100 B1 * | 3/2017 | Ware | G06F 16/90324 |
| 9,691,096 B1 * | 6/2017 | Dai | G06Q 30/0631 |
| 9,720,974 B1 * | 8/2017 | Sarmento | G06F 16/24573 |
| 9,978,070 B1 * | 5/2018 | Peterson | G06Q 30/01 |
| 10,237,294 B1 * | 3/2019 | Zadeh | H04L 63/1425 |
| 2006/0093190 A1 * | 5/2006 | Cheng | G06K 9/00771 382/115 |
| 2008/0319796 A1 * | 12/2008 | Stivoric | A61B 5/6802 705/3 |
| 2012/0054194 A1 * | 3/2012 | Gao | G06K 9/00744 707/741 |
| 2013/0055367 A1 * | 2/2013 | Kshirsagar | G06F 21/316 726/6 |
| 2018/0001184 A1 * | 1/2018 | Tran | A63B 43/004 |
| 2018/0174229 A1 * | 6/2018 | Sherwin | G06F 9/451 |
| 2019/0147218 A1 * | 5/2019 | Johnson | G06K 9/00087 |

* cited by examiner

*Primary Examiner* — Tauqir Hussain

(74) *Attorney, Agent, or Firm* — Caldwell Intellectual Propert

(57) ABSTRACT

A system for using artificial intelligence to select a recommended compatible element. The system includes at least a server, wherein the at least a server is designed and configured to receive training data. The at least a server is configured to receive from a user at least a biological extraction and at least a user activity datum. The at least a server is configured to retrieve from a fingerprint database at least a datum of user fingerprint information. The at least a server is configured to classify the at least a user activity datum as a function of the at least a datum of user fingerprint information. The at least a server is configured to select at least a compatible element as a function of the at least a user activity datum and the training data. The at least a server is configured to transmit the at least a compatible element to a user client device.

16 Claims, 17 Drawing Sheets

Compatible Element Similarity Index Value Database 1500

- Beauty Table 1504
- Books Table 1508
- Electronics Table 1512
- Grocery & Gourmet Foods Table 1516
- Home & Garden Table 1520
- Music Table 1524

FIG. 15

METHODS AND SYSTEMS FOR USING ARTIFICIAL INTELLIGENCE TO ANALYZE USER ACTIVITY DATA

FIELD OF THE INVENTION

The present invention generally relates to the field of artificial intelligence. In particular, the present invention is directed to methods and systems for using artificial intelligence to analyze user activity data.

BACKGROUND

Accurate selection of compatible elements can be challenging. Accurately selection and recommendation of compatible elements is of utmost importance. Incorrect selection of compatible elements can lead to error and user frustration.

SUMMARY OF THE DISCLOSURE

In an aspect, a system for using artificial intelligence to analyze user activity data. The system includes at least a server. At least a server is configured to receive training data, wherein receiving training data further comprises receiving a training set including a plurality of first data entries, each first data entry of the plurality of first data entries including at least an element of physiological state data and at least a correlated compatible label. At least a server is configured to receive, from a user, at least a biological extraction and at least a user activity datum. At least a server is configured to retrieve, from a fingerprint database, at least a datum of user fingerprint information. At least a server is configured to classify the at least a user activity datum as a function of the at least a datum of user fingerprint information. At least a server is configured to select at least a compatible element as a function of the at least a user activity datum and the training data. At least a server is configured to transmit the at least a compatible element to a user client device.

In an aspect, a method of using artificial intelligence to analyze user activity data. The method includes receiving by at least a server training data, wherein receiving training data further comprises receiving a training set including a plurality of first data entries, each first data entry of the plurality of first data entries including at least an element of physiological state data and at least a correlated compatible label. The method includes receiving by the at least a server at least a biological extraction and at least a user activity datum from a user. The method includes retrieving by the at least a server at least a datum of user fingerprint information from a fingerprint database. The method includes classifying by the at least a server the at least a user activity datum as a function of the at least a datum of user fingerprint information. The method includes selecting by the at least a server at least a compatible element as a function of the at least a user activity datum and the training data. The method includes transmitting by the at least a server the at least a compatible element to a user client device.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 15 is a block diagram illustrating an exemplary embodiment of a compatible element similarity index value database;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for using artificial intelligence to select a recommended compatible element. In an embodiment, at least a server receives at least a biological extraction from a user and at least a user activity datum. At least a server retrieves from a fingerprint database at least a datum of user fingerprint information. User fingerprint information may include for example a previous user activity datum. User fingerprint information may include previous search queries that a user may have generated. At least a server classifies the at least a user activity datum. Classification may be customized to a particular user and based on a particular user's fingerprint information. At least a server selects at least a compatible element. At least a compatible element is then transmitted by at least a server to a user client device.

Figure 1:
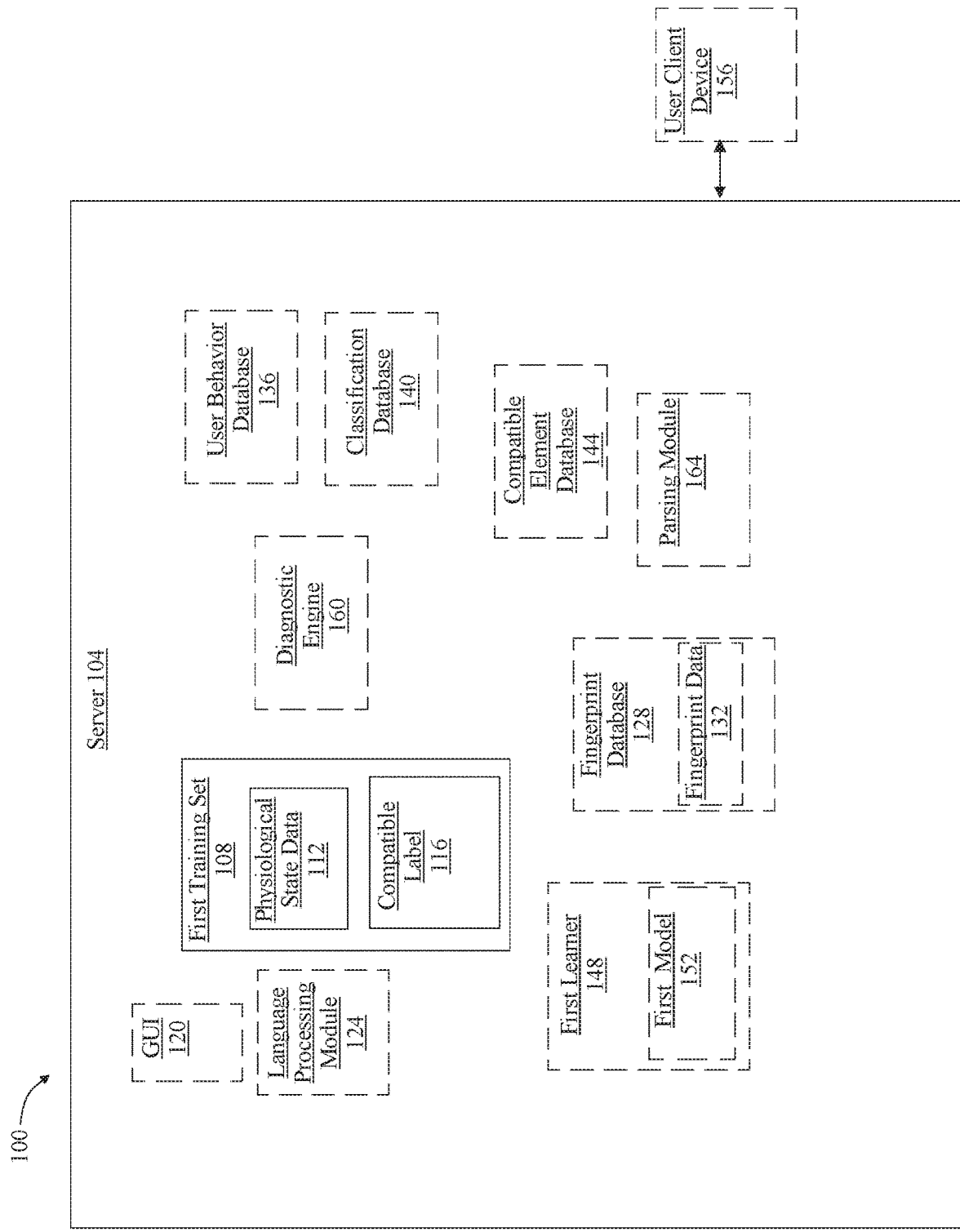
FIG. 1 is a block diagram illustrating an exemplary embodiment of a system for using artificial intelligence to analyze user activity data.

Turning now to FIG. 1, an exemplary embodiment of a system 100 for using artificial intelligence to analyze user activity data is illustrated. System 100 includes at least a server 104. At least a server 104 may include any computing device as described herein, including without limitation a microcontroller, microprocessor, digital signal processor (DSP) and/or system on a chip (SoC) as described herein. At least a server 104 may be housed with, may be incorporated in, or may incorporate one or more sensors of at least a sensor. Computing device may include, be included in, and/or communicate with a mobile device such as a mobile telephone or smartphone. At least a server 104 may include a single computing device operating independently, or may include two or more computing device operating in concert, in parallel, sequentially or the like; two or more computing devices may be included together in a single computing device or in two or more computing devices. At least a server 104 with one or more additional devices as described below in further detail via a network interface device. Network interface device may be utilized for connecting a at least a server 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. At least a server 104 may include but is not limited to, for example, a at least a server 104 or cluster of computing devices in a first location and a second computing device or cluster of computing devices in a second location. At least a server 104 may include one or more computing devices dedicated to data storage, security, distribution of traffic for load balancing, and the like. At least a server 104 may distribute one or more computing tasks as described below across a plurality of computing devices of computing device, which may operate in parallel, in series, redundantly, or in any other manner used for distribution of tasks or memory between computing devices. At least a server 104 may be implemented using a "shared nothing" architecture in which data is cached at the worker, in an embodiment, this may enable scalability of system 100 and/or computing device.

With continued reference to FIG. 1, at least a server 104 is configured to receive training data. Training data, as used herein, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name and/or a description of a medical condition or therapy may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below.

With continued reference to FIG. 1, at least a server 104 is configured to receive a first training set 108 including a plurality of first data entries, each first data entry of the first training set 108 including at least an element of physiological state data 112 and at least a correlated compatible label. At least an element of physiological state data 112 as used herein, includes any data indicative of a person's physiological state. A compatible label as used herein, includes any identifier of any compatible element that is compatible with a user. Compatible element, as used herein, includes one or more products, ingredients, merchandise, additive, component compound, mixture, constituent, element, article, and/or information content that is compatible with a user as described in more detail below. At least an element of physiological state data 112 may include any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. Physiological state data 112 may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data 112 may include, without limitation, immune function data such as Interleukine-6 (IL-6), TNF-alpha, systemic inflammatory cytokines, and the like.

Continuing to refer to FIG. 1, physiological state data 112 may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data 112 may include measures of glucose metabolism such as fasting glucose levels and/or hemoglobin A1-C(HbA1c) levels. Physiological state data 112 may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data 112 may include measures of estimated glomerular filtration rate (eGFR). Physiological state data 112 may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline phosphatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data 112 may include antinuclear antibody levels. Physiological state data 112 may include aluminum levels. Physiological state data 112 may include arsenic levels. Physiological state data 112 may include levels of fibrinogen, plasma cystatin C, and/or brain natriuretic peptide.

Continuing to refer to FIG. 1, physiological state data 112 may include measures of lung function such as forced expiratory volume, one second (FEV-1) which measures how much air can be exhaled in one second following a deep inhalation, forced vital capacity (FVC), which measures the volume of air that may be contained in the lungs. Physiological state data 112 may include a measurement blood pressure, including without limitation systolic and diastolic blood pressure. Physiological state data 112 may include a measure of waist circumference. Physiological state data 112 may include body mass index (BMI). Physiological state data 112 may include one or more measures of bone mass and/or density such as dual-energy x-ray absorptiometry. Physiological state data 112 may include one or more measures of muscle mass. Physiological state data 112 may include one or more measures of physical capability such as without limitation measures of grip strength, evaluations of standing balance, evaluations of gait speed, pegboard tests, timed up and go tests, and/or chair rising tests.

Still viewing FIG. 1, physiological state data 112 may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data 112 may include one or more measures of psychological function or state, such as without limitation clinical interviews, assessments of intellectual functioning and/or intelligence quotient (IQ) tests, personality assessments, and/or behavioral assessments. Physiological state data 112 may include one or more psychological self-assessments, which may include any self-administered and/or automatedly computer-administered assessments, whether administered within system 100 and/or via a third-party service or platform.

Continuing to refer to FIG. 1, physiological state data 112 may include psychological data. Psychological data may include any data generated using psychological, neuropsychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing module 144 as described in this disclosure.

With continued reference to FIG. 1, physiological state data 112 may include one or more evaluations of sensory ability, including measures of audition, vision, olfaction, gustation, vestibular function and pain. Physiological state data 112 may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data 112 may include proteomic data, which as used herein, is data describing all proteins produced and/or modified by an organism, colony of organisms, or system of organisms, and/or a subset thereof. Physiological state data 112 may include data concerning a microbiome of a person, which as used herein, includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data 112 of a person, and/or on compatible label and/or ameliorative processes as described in further detail below. Physiological state data 112 may include any physiological state data 112, as described above, describing any multicellular organism living in or on a person including any parasitic and/or symbiotic organisms living in or on the persons; non-limiting examples may include mites, nematodes, flatworms, or the like.

With continuing reference to FIG. 1, physiological state data 112 may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Examples of physiological state data 112 described in this disclosure are presented for illustrative purposes only and are not meant to be exhaustive. Persons skilled in the art, upon reviewing the entirety of this disclosure, will be aware of various additional examples of physiological state data 112 that may be used consistently with descriptions of systems and methods as provided in this disclosure.

With continued reference to FIG. 1, each element of first training set 108 includes at least a correlated compatibility label 116. A correlated compatibility label, as described herein, is an element of data identifying and/or describing any product, ingredient, element, merchandise, additive, component, compound, mixture, constituent, element, article, and/or information content that is compatible with a user as a function of a user's biological extraction. A product may include for example, goods such as but not limited to beauty products, books, electronics, art, food and grocery, health and personal goods, home and garden, appliances, music, office goods, outdoor goods, sporting goods, tools, toys, home improvement, video, digital versatile disc (DVD), blue-ray, jewelry, musical instruments, computers, cell phones, movies, and the like.

With continued reference to FIG. 1, a correlated compatibility label 116 may be associated with one or more elements of physiological state data 112. For example, a correlated compatibility label for a product such as shampoo containing parabens may be associated with one or more biological extractions including Apolipoprotein E Gene 2 (APOE2) and Apolipoprotein E Gene 3 (APOE3) and not Apolipoprotein E Gene 4 (APOE4). In yet another non-limiting example, a correlated compatibility label for a product containing dextromethorphan may be associated with one or more elements of physiological data including gene profiles such as extensive metabolizers and ultra-rapid metabolizers and not poor metabolizer. In yet another non-limiting example, a correlated compatibility label for literature describing the benefits of melatonin in breast cancer treatment may be associated with one or more elements of physiological data including positive test results indicating a current breast cancer diagnosis, as well as biological extractions indicating the presence of the breast cancer gene 1 (BRCA1), breast cancer gene 2 (BRCA2), and cyclin-dependent kinase inhibitor 1B gene (CDKN1B). In yet another non-limiting example, a correlated advisory label for a product containing classical music may be associated with one or more elements of physiological data including a positive pregnancy test, a positive evaluation for anxiety, and a positive evaluation for depression. In yet another non-limiting example, a correlated advisory label for organic makeup may be associated with one or more elements of physiological data including an elevated thyroid stimulating hormone (TSH), an elevated c-reactive protein (CRP), and an elevated erythrocyte sedimentation rate (ESR).

With continued reference to FIG. 1, correlated compatibility label 116 may be stored in any suitable data and/or data type. For instance, and without limitation, correlated compatibility label may include textual data, such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as at least a compatibility label may take; persons skilled in the art, upon reviewing the entirety of this disclosure, will be aware of various forms which may be suitable for use as at least an advisory label consistently with this disclosure.

With continued reference to FIG. 1, correlated compatibility label 116 may be stored as image data, such as for example an image of a particular product such as a photograph of a particular sunscreen product or an image of a particular book. Image data may be stored in various forms including for example, joint photographic experts group (JPEG), exchangeable image file format (Exif), tagged image file format (TIFF), graphics interchange format (GIF), portable network graphics (PNG), netpbm format, portable bitmap (PBM), portable any map (PNM), high efficiency image file format (HEIF), still picture interchange file format (SPIFF), better portable graphics (BPG), drawn filed, enhanced compression wavelet (ECW), flexible image transport system (FITS), free lossless image format (FLIF), graphics environment manage (GEM), portable arbitrary map (PAM), personal computer exchange (PCX), progressive graphics file (PGF), gerber formats, 2 dimensional vector formats, 3 dimensional vector formats, compound formats including both pixel and vector data such as encapsulated postscript (EPS), portable document format (PDF), and stereo formats.

With continued reference to FIG. 1, in each first data element of first training set 108 at least an element of physiological state data 112 is correlated with a compatible label 116 where the element of physiological data is located in the same data element and/or portion of data element as the compatible label; for example, and without limitation, an element of physiological data is correlated with a correlated element where both element of physiological data and correlated element are contained within the same first data element of the first training set. As a further example, an element of physiological data is correlated with a correlated element where both share a category label as described in further detail below, where each is within a certain distance of the other within an ordered collection of data in data element, or the like. Still further, an element of physiological data may be correlated with a correlated element where the element of physiological data and the correlated element share an origin, such as being data that was collected with regard to a single person or the like. In an embodiment, a first datum may be more closely correlated with a second datum in the same data element than with a third datum contained in the same data element; for instance, the first element and the second element may be closer to each other in an ordered set of data than either is to the third element, the first element and second element may be contained in the same subdivision and/or section of data while the third element is in a different subdivision and/or section of data, or the like. Persons skilled in the art, upon reviewing the entirety of this disclosure, will be aware of various forms and/or degrees of correlation between physiological data and compatible label that may exist in first training set 108 and/or first data element consistently with this disclosure.

With continued reference to FIG. 1, at least a server 104 may be designed and configured to associate at least an element of physiological state data 112 with at least a category from a list of significant categories of physiological state data 112. Significant categories of physiological state data 112 may include labels and/or descriptors describing types of physiological state data 112 that are identified as being of high relevance in identifying compatible label. As a non-limiting example, one or more categories may identify significant categories of physiological state data 112 based on degree of diagnostic relevance to one or more impactful conditions and/or within one or more medical or public health fields. For instance, and without limitation, a particular set of biomarkers, test results, and/or biochemical information may be recognized in a given medical field as useful for identifying various disease conditions or associated ingredients and products that may be compatible with a particular disease or condition as well as associated ingredients and products that may not be compatible with a particular disease or condition. As a non-limiting example, and without limitation, physiological data describing disorders associated with heavy metal accumulation including for example heart disease, Lyme disease, and Multiple Sclerosis may be useful in selecting compatible label that include organic ingredients free of heavy metals such as lead, mercury, arsenic, cadmium, and chromium. As an additional example, physiological data associated with mental disorders such as anxiety, bipolar disorder, depression, and schizophrenia may be useful in selecting compatible label that include music products with calming music such as classical music, smooth jazz, blues, and elevator music. In a further non-limiting example, physiological data describing disorders such as an allergic dermatitis to certain metals such as nickel or lead may be useful in selecting compatible label that include jewelry that is free of such ingredients. Persons skilled in the art, upon reviewing the entirety of this disclosure, will be aware of various additional categories of physiological data that may be used consistently with this disclosure.

Still referring to FIG. 1, at least a server 104 may receive the list of significant categories according to any suitable process; for instance, and without limitation, at least a server 104 may receive the list of significant categories from at least an expert. In an embodiment, at least a server 104 may provide a graphical user interface, which may include without limitation a form or other graphical element having data entry fields, wherein one or more experts, including without limitation clinical and/or scientific experts, may enter information describing one or more categories of physiological data that the experts consider to be significant or useful for detection of conditions; fields in graphical user interface may provide options describing previously identified categories, which may include a comprehensive or near-comprehensive list of types of physiological data detectable using known or recorded testing methods, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface 120 or the like may include fields corresponding to compatible label, where experts may enter data describing compatible label and/or categories of compatible label the experts consider related to entered categories of physiological data; for instance, such fields may include drop-down lists or other pre-populated data entry fields listing currently recorded compatible label, and which may be comprehensive, permitting each expert to select a compatible label and/or a plurality of compatible label the expert believes to be predicted and/or associated with each category of physiological data selected by the expert. Fields for entry of compatible label and/or categories of compatible label may include free-form data entry fields such as text entry fields; as described above, examiners may enter data not presented in pre-populated data fields in the free-form data entry fields. Training data may be sorted or filtered according to "categories" or "significance scores" whereby training data may be trimmed to categories that are most significant and/or most closely related to a given user's categories. Categories may be used to trim or sort training data according to domain limitations. Expert input and/or other input of categories including any of the categories as described herein, can creating training data entries where categories are a label such as a physiological label or compatible label, and associations between them may be used to create correlations. Categories that are discovered or defined by any process may become labels such as physiological labels or compatible labels of the sorts of things they are related to, in the training data. Data may be received, a category may be associated with it to create a first kind of label, and a second category may be associated to create a second kind of label, thereby creating a training data entry. Alternatively or additionally, fields for entry of compatible label may enable an expert to select and/or enter information describing or linked to a category of compatible label that the expert considers significant, where significance may indicate likely impact on longevity, mortality, quality of life, or the like as described in further detail below. Graphical user interface 120 may provide an expert with a field in which to indicate a reference to a document describing significant categories of physiological data, relationships of such categories to compatible label, and/or significant categories of compatible label. Any data described above may alternatively or additionally be received from experts similarly organized in paper form, which may be captured and entered into data in a similar way, or in a textual form such as a portable document file (PDF) with examiner entries, or the like. Outputs of each machine-learning process may have associated "categories" and may be sorted or filtered according to "categories" including prior to use as inputs to subsequent machine-learning processes.

With continued reference to FIG. 1, data information describing significant categories of physiological data, relationships of such categories to compatible label, and/or significant categories of compatible label may alternatively or additionally be extracted from one or more documents using a language processing module 124. Language processing module 124 may include any hardware and/or software module. Language processing module 124 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module 124 may compare extracted words to categories of physiological data recorded by at least a server 104, one or more compatible label recorded by at least a server 104, and/or one or more categories of compatible label recorded by at least a server 104; such data for comparison may be entered on at least a server 104 as described above using expert data inputs or the like. In an embodiment, one or more categories may be enumerated, to find total count of mentions in such documents. Alternatively or additionally, language processing module may operate to produce a language processing model. Language processing model 124 may include a program automatically generated by at least a server 104 and/or language processing module 124 to produce associations between one or more words extracted from at least a document and detect associations, including without limitation mathematical associations, between such words, and/or associations of extracted words with categories of physiological data, relationships of such categories to compatible label, and/or categories of compatible label. Associations between language elements, where language elements include for purposes herein extracted words, categories of physiological data, relationships of such categories to compatible label, and/or categories of compatible label may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of physiological data, a given relationship of such categories to compatible label, and/or a given category of compatible label. As a further example, statistical correlations and/or mathematical associations may include probabilistic formulas or relationships indicating a positive and/or negative association between at least an extracted word and/or a given category of physiological data, a given relationship of such categories to compatible label, and/or a given category of compatible label; positive or negative indication may include an indication that a given document is or is not indicating a category of physiological data, relationship of such category to compatible label, and/or category of compatible label is or is not significant. For instance, and without limitation, a negative indication may be determined from a phrase such as "phthalates were not found to increase the risk of testicular cancer," whereas a positive indication may be determined from a phrase such as "phthalates were found to increase the risk of breast cancer," as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory by at least a server 104, or the like.

Still referring to FIG. 1, language processing module 124 and/or at least a server 104 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein, are statistical models with inference algorithms that that may be applied to the models. In such models, a hidden state to be estimated may include an association between an extracted word category of physiological data, a given relationship of such categories to compatible label, and/or a given category of compatible label. There may be a finite number of category of physiological data, a given relationship of such categories to compatible label, and/or a given category of compatible label to which an extracted word may pertain; an HMM inference algorithm, such as the forward-backward algorithm or the Viterbi algorithm, may be used to estimate the most likely discrete state given a word or sequence of words. Language processing module 124 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model 124 may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module 124 may use a corpus of documents to generate associations between language elements in a language processing module and at least a server 104 may then use such associations to analyze words extracted from one or more documents and determine that the one or more documents indicate significance of a category of physiological data, a given relationship of such categories to compatible label, and/or a given category of compatible label. In an embodiment, at least a server 104 may perform this analysis using a selected set of significant documents, such as documents identified by one or more experts as representing good science, good clinical analysis, or the like; experts may identify or enter such documents via graphical user interface, or may communicate identities of significant documents according to any other suitable method of electronic communication, or by providing such identity to other persons who may enter such identifications into at least a server 104. Documents may be entered into at least a server 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, at least a server 104 may automatically obtain the document using such an identifier, for instance by submitting a request to a database or compendium of documents such as JSTOR as provided by Ithaka Harbors, Inc. of New York.

Continuing to refer to FIG. 1, whether an entry indicating significance of a category of physiological data, a given relationship of such categories to compatible label, and/or a given category of compatible label is entered via graphical user interface, alternative submission means, and/or extracted from a document or body of documents as described above, an entry or entries may be aggregated to indicate an overall degree of significance. For instance, each category of physiological data, relationship of such categories to compatible label, and/or category of compatible label may be given an overall significance score; overall significance score may, for instance, be incremented each time an expert submission and/or paper indicates significance as described above. Persons skilled in the art, upon reviewing the entirety of this disclosure will be aware of other ways in which scores may be generated using a plurality of entries, including averaging, weighted averaging, normalization, and the like. Significance scores may be ranked; that is, all categories of physiological data, relationships of such categories to compatible label, and/or categories of compatible label may be ranked according significance scores, for instance by ranking categories of physiological data, relationships of such categories to compatible label, and/or categories of compatible label higher according to higher significance scores and lower according to lower significance scores. Categories of physiological data, relationships of such categories to compatible label, and/or categories of compatible label may be eliminated from current use if they fail a threshold comparison, which may include a comparison of significance score to a threshold number, a requirement that significance score belong to a given portion of ranking such as a threshold percentile, quartile, or number of top-ranked scores. Significance scores may be used to filter outputs as described in further detail below; for instance, where a number of outputs are generated and automated selection of a smaller number of outputs is desired, outputs corresponding to higher significance scores may be identified as more probable and/or selected for presentation while other outputs corresponding to lower significance scores may be eliminated. Alternatively or additionally, significance scores may be calculated per sample type; for instance, entries by experts, documents, and/or descriptions of purposes of a given type of physiological test or sample collection as described above may indicate that for that type of physiological test or sample collection a first category of physiological data, relationship of such category to compatible label, and/or category of compatible label is significant with regard to that test, while a second category of physiological data, relationship of such category to compatible label, and/or category of compatible label is not significant; such indications may be used to perform a significance score for each category of physiological data, relationship of such category to compatible label, and/or category of compatible label is or is not significant per type of physiological sample, which then may be subjected to ranking, comparison to thresholds and/or elimination as described above.

Still referring to FIG. 1, at least a server 104 may detect further significant categories of physiological data, relationships of such categories to compatible label, and/or categories of compatible label using machine-learning processes, including without limitation unsupervised machine-learning processes as described in further detail below; such newly identified categories, as well as categories entered by experts in free-form fields as described above, may be added to pre-populated lists of categories, lists used to identify language elements for language learning module, and/or lists used to identify and/or score categories detected in documents, as described above. Unsupervised machine-learning processes that identify associations may also create training data sets by creating new categories and creating data entries associating them to each other. Unsupervised machine-learning processes may identify associations such as by creating new categories and allowing experts to identify associations. Unsupervised machine-learning processes may identify associations such as by obtaining associations from documents linking two newly derived categories together.

Continuing to refer to FIG. 1, in an embodiment, at least a server 104 may be configured, for instance as part of receiving the first training set, to associate at least a correlated first compatible label with at least a category from a list of significant categories of compatible label. Significant categories of compatible label may be acquired, determined, and/or ranked as described above. As a non-limiting example, compatible label may be organized according to relevance to and/or association with a list of significant conditions. A list of significant conditions may include, without limitation, conditions having generally acknowledged impact on longevity and/or quality of life; this may be determined, as a non-limiting example, by a product of relative frequency of a condition within the population with years of life and/or years of able-bodied existence lost, on average, as a result of the condition. A list of conditions may be modified for a given person to reflect a family history of the person; for instance, a person with a significant family history of a particular condition or set of conditions, or a genetic profile having a similarly significant association therewith, may have a higher probability of developing such conditions than a typical person from the general population, and as a result at least a server 104 may modify list of significant categories to reflect this difference.

With continued reference to FIG. 1, at least a server 104 is configured to receive at least a biological extraction from a user. At least a biological extraction, as used herein, includes may include any element and/or elements of data suitable for use as an element of physiological state data 112. At least a biological extraction may include a physically extracted sample, which as used herein includes a sample obtained by removing and analyzing tissue and/or fluid. Physically extracted sample may include without limitation a blood sample, a tissue sample, a buccal swab, a mucous sample, a stool sample, a hair sample, a fingernail sample, or the like. Physically extracted sample may include, as a non-limiting example, at least a blood sample. As a further non-limiting example, at least a biological extraction may include at least a genetic sample. At least a genetic sample may include a complete genome of a person or any portion thereof. At least a genetic sample may include a DNA sample and/or an RNA sample. At least a biological extraction may include an epigenetic sample, a proteomic sample, a tissue sample, a biopsy, and/or any other physically extracted sample. At least a biological extraction may include an endocrinal sample. As a further non-limiting example, the at least a biological extraction may include a signal from at least a sensor configured to detect physiological data of a user and recording the at least a biological extraction as a function of the signal. At least a sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MM) equipment, ultrasound equipment, optical scanning equipment such as photo-plethysmographic equipment, or the like. At least a sensor may include any electromagnetic sensor, including without limitation electroencephalographic sensors, magnetoencephalographic sensors, electrocardiographic sensors, electromyographic sensors, or the like. At least a sensor may include a temperature sensor. At least a sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. At least a sensor may detect any hematological parameter including blood oxygen level, pulse rate, heart rate, pulse rhythm, and/or blood pressure. At least a sensor may be a part of at least a server 104 or may be a separate device in communication with at least a server 104.

Still referring to FIG. 1, at least a biological extraction may include any data suitable for use as physiological state data 112 as described above, including without limitation any result of any medical test, physiological assessment, cognitive assessment, psychological assessment, or the like. System 100 may receive at least a biological extraction from one or more other devices after performance; system 100 may alternatively or additionally perform one or more assessments and/or tests to obtain at least a biological extraction, and/or one or more portions thereof, on system 100. For instance, at least biological extraction may include or more entries by a user in a form or similar graphical user interface object; one or more entries may include, without limitation, user responses to questions on a psychological, behavioral, personality, or cognitive test. For instance, at least a server 104 may present to user a set of assessment questions designed or intended to evaluate a current state of mind of the user, a current psychological state of the user, a personality trait of the user, or the like; at least a server 104 may provide user-entered responses to such questions directly as at least a biological extraction and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

Alternatively or additionally, and with continued reference to FIG. 1, at least a biological extraction may include assessment and/or self-assessment data, and/or automated or other assessment results, obtained from a third-party device; third-party device may include, without limitation, a server 104 or other device (not shown) that performs automated cognitive, psychological, behavioral, personality, or other assessments. Third-party device may include a device operated by an informed advisor such a functional health care professional including for example a functional medicine doctor.

Still referring to FIG. 1, at least a biological extraction may include data describing one or more test results, including results of mobility tests, stress tests, dexterity tests, endocrinal tests, genetic tests, and/or electromyographic tests, biopsies, radiological tests, genetic tests, and/or sensory tests. At least a server 104 may be configured to record at least a biological extraction from a user. Persons skilled in the art, upon reviewing the entirety of this disclosure, will be aware of various additional examples of at least a biological extraction consistent with this disclosure.

With continued reference to FIG. 1, at least a server 104 is configured to receive at least a user activity datum data from a user. A user activity datum as used herein, includes any data describing a user's behaviors or actions performed by the user when searching for items and products contained within system 100. Items and/or products as used herein, include any physical item of manufacture, a media item, a digital item, and/or a service or other item for purchase or selection contained within a networked environment. Items and/or products may be categorized into categories such as beauty, books, business products, camera and photo, electronics, clothing, jewelry, fine art, grocery and gourmet food, health and personal care, home and garden, luggage, travel accessories, music, musical instruments, office products, shoes, handbags, sports, tools, sports, watches, and the like. Items and/or products may include for example shampoo, toothpaste, books, pens, body wash, cars, computers, tablets, flowers, plants, garden equipment, food products such as chips, candy, cookies, protein bars, and the like. At least a user activity datum data may include browsing history of compatible elements that user may have created a search query for. A search query as used herein, includes any search word and/or phrases that a user may enter into a search engine when browsing for a particular item and/or product. A search query may include a word and/or string of words describing a particular category of products such as "automobile parts" or "women's handbags." In yet another non-limiting example, a search query may include a word and/or string of words describing a particular product and/or item such as "unscented hand lotion" or "organic potato chips." At least a user activity datum data may include a term describing a particular product or compatible element that a user may be looking for. For example, a user may generate a search query to find compatible elements relating to electronics that contains a query such as "cell phones" or "computers." At least a user activity datum data may include a reformulated search query such as deletion of a term, reformulation of the query, a term swap, a term addition, a scope change, a refinement of the search query and the like. For example, at least a user activity datum data may include a reformulated search query such as an original search query that includes "computer accessory" that is reformulated to include "computer laptop cover." At least a user activity datum data may include the selection of an item such as by clicking on a product to learn more about that particular item. For example, a user may click on a product such as a shampoo to be taken to a product detail page to learn more about the shampoo such as to read the ingredients contained within the shampoo, the scent of the shampoo, the directions for how to use the shampoo, and the like. At least a user activity datum data may include an abandonment query such as when a user may enter a query but abandon searching for the query by not selecting a search button or search selection.

With continued reference to FIG. 1, at least a server 104 is configured to retrieve from a fingerprint database 128 at least a datum of user fingerprint information. Fingerprint database 128 is described in more detail below in reference to FIG. 7. User fingerprint information as used herein, is any data identifying one or more actions performed by a user in relation to a search query during a search session. For example, user fingerprint information may include data describing several search queries that a user entered over the course of a period of time such as over the course of five days. In yet another non-limiting example, user fingerprint information may include a timestamp that includes data describing a date and/or time when user entered a particular search query. In yet another non-limiting example, timestamp may include data describing how long a user searched for products and/or items within a particular search query or how long a user looked at more information describing a particular product contained within a search query. For example, a search query for "flat screen television" may generate twenty webs pages of results and fingerprint information may include data describing how long a user spent examining twenty web pages and how long a user spent looking and clicking through particular products listed on the twenty pages. User fingerprint data 132 may include data describing previous purchases that a user made such as for example a particular makeup product that a user purchased seven times in one year or a particular snack product that a user purchased twice in one week. In an embodiment, user fingerprint information may include fingerprint information that is specific to a single user. In an embodiment, user fingerprint information may include fingerprint information that is specific to a plurality of users. In an embodiment, user fingerprint information may include fingerprint information that is specific to a particular group of users such as users living in the same household or users with similar diagnostic outputs or biological extraction results as described in more detail below in reference to FIG. 2.

With continued reference to FIG. 1, at least a server 104 may be configured to retrieve from a behavior database 136 at least a datum of user behavior data. Behavior database 136 is described in more detail below in reference to FIG. 8. User behavior data, as used herein, is any data identifying one or more user behaviors in relation to purchasing any item and/or product contained within system 100. User behavior data may include purchasing history of certain items and/or products contained within system 100. For example, user behavior data may include an item that a user previously purchased and then returned. User behavior data may include an item and/or product that a user purchased more than once during a specific period of time. In yet another non-limiting example, user behavior data may include an item that a user repeatedly purchased over a certain period of time such as a toothpaste that a user bought four times in the past two months. User behavior data may include information describing categories of items and/or products that a user purchased over a certain period of time. For example, user behavior data may include all shoes that a user purchased over the past three years or all health and personal care items that user purchased over the past six months. User behavior data may include information describing same product that a user purchased but manufactured and/or produced by a separate manufacturer. For example, a user may have previously purchased a particular brand of laundry detergent four months ago and then repurchased a different brand of laundry detergent three months ago.

With continued reference to FIG. 1, at least a server 104 is configured to classify the at least a user activity datum as a function of the at least a datum of user fingerprint information. Classification as used herein, includes any element of data identifying and/or describing a category of a user activity datum. Category may include a class of search queries having particular shared characteristics. At least a user activity datum and/or a search query may be classified as "broad inquiry" such as when at least a user activity datum includes a request for a category of items and/or products such as "garden equipment" or "automobiles." At least a user activity datum and/or a search query may be classified as "brand inquiry" such as when at least a user activity datum includes a request for a specific brand of items and/or products such as "Belkin surge protector" or "Apple iPad." At least a user activity datum and/or a search query may be classified as "defined inquiry" such as when at least a user activity datum includes a request for a defined item and/or product that may be contained within a category of products and/or items but may not necessarily include a request for a particular brand or manufacturer. For example, at least a user activity datum and/or a search query may include a request for "smart keyboards" or "eyeshadow." Classification information such as categories and/or classification labels may be contained within a classification database 140. Classification database 140 is described in more detail below in reference to FIG. 9.

With continued reference to FIG. 1, at least a server 104 may be configured to classify the at least a user activity datum function by matching the at least a datum of user fingerprint information to at least a datum of previous user activity. Datum of previous user activity, as used herein includes any action performed by a user in relation to at least a user activity datum. For example, datum of previous user activity may include an item and/or product that a user may have selected to discover more information about or a specific search query that a user repeatedly entered. Datum of previous user activity may include timestamp information including any of the timestamp information as described above. For example a datum of previous user activity that includes a short search session related to a query may be indicative of few modifications to a search query whereas a long search session related to a query may be indicative of multiple modifications.

With continued reference to FIG. 1, at least a server 104 may be configured to classify the at least a user activity datum as a function of receiving at least a datum of modified user activity data. Modified user activity, as used herein, includes any user activity datum that has been modified after first entry. Modified may include without limitation, a reformulation of the at least a user activity datum, a term swap, a term addition, a term deletion, an abandonment of the user activity datum, a refinement of the user activity datum, a scope change, and the like. For example, a modified user activity may include a user activity datum that includes a search query for a "bicycle" which is searched and then narrowed in scope to include "bicycle for three year old girl." In yet another non-limiting example, modified user activity may include a user activity datum that includes a search query for "dishwasher soap" that is then modified to add a term to read "natural dishwasher soap." In yet another non-limiting example, a modified user activity may include a user activity datum that includes a search query for "men's size 11 tennis shoes" that is then modified to delete a term to read "men's size 11 shoes."

With continued reference to FIG. 1, at least a server 104 is configured to select at least a compatible element as a function of the at least a user activity datum and the training data. A compatible element may include any of the compatible elements as described above. A compatible element may include for example one or more products, ingredients, merchandise, additive, component compound, mixture, constituent, element, article, and/or information content that is compatible with a user. A compatible element may include a particular brand of product, a particular ingredient contained within a product, a particular category of products, a particular category of ingredients, a particular product line, a particular ingredient line. For example, a compatible element may include a shampoo that contains ingredients that won't cause user's seborrheic eczema to flare up. In yet another non-limiting example, a compatible element may include a list of music artists that won't worsen a user's intermittent explosive disorder. In yet another non-limiting example, a compatible element may include a list of makeup free of mold for a user with mold toxicity. In yet another non-limiting example, compatible element may contain a list of cleaning products free of gluten for a user with Celiac Disease. Compatibility includes one or more products, ingredients, merchandise, additive, component compound, mixture, constituent, element, article, and/or informational content that is capable of use and/or consumption by a user without an adverse effect. An adverse effect may include any negative effect on longevity, health condition, mortality, and/or quality of life of a user. For example, a user with dermatitis herpetiformis who uses hand soap containing gluten may experience an adverse response such as a blistering rash on body parts exposed to gluten containing hand soap. In yet another non-limiting example, a user with small intestinal bacterial overgrowth (SIBO) who consumes kombucha rich in microorganisms may experience an adverse response such as bloating, gas, and diarrhea. In yet another non-limiting example, a user with breast cancer susceptibility gene (BRCA 1 or BRCA 2) who uses personal care items containing phthalates may experience an adverse effect such as a greater risk of developing breast cancer. In an embodiment, a compatible element containing a plurality of products and/or ingredients may be ranked in order of compatibility. For example, a compatible element containing three shampoos that may be suitable for use by a user with a lactose allergy may be listed in order of compatibility from most compatible down to least compatible. In such an instance, products and/or ingredients may be ranked such as for example most compatible if a product was manufactured in a certified lactose free facility whereas a product may be ranked least compatible if it was manufactured in a facility that doesn't use lactose as an ingredient but is not a certified lactose free facility. Rankings and order of compatibility may be customized around a user's individual needs whereby one product for a user with celiac disease that is certified gluten free may be highly ranked for one user while that same product may be least compatible for a user with a corn allergy because it is not manufactured in a certified corn free facility. Compatible elements may be contained within a compatible element database 144 as described in more detail below in reference to FIG. 15.

With continued reference to FIG. 1, at least a server 104 may be configured to select at least a compatible element using a machine-learning algorithm and the training set. System 100 may include a first label learner operating at least a server. First label learner may be designed and configured to select at least a compatible element using a first machine-learning algorithm and the first training data relating physiological data to compatible label. At least a first machine-learning model 152 may include one or more models that determine a mathematical relationship between physiological data and compatible label. Such models may include without limitation model developed using linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 1, machine-learning algorithm used to generate first machine-learning model 152 may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 1, first label learner may generate compatibility output using alternatively or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using first training set; the trained network may then be used to apply detected relationships between elements of physiological state data and compatible label.

With continued reference to FIG. 1, at least a server 104 may select at least a compatible element as a function of a compatible element category. Compatible element category, as used herein is an element of data which identifies a compatible element having particular shared characteristics. Shared characteristics may include traits, and/or qualities that identify a compatible element as being uses for a particular purpose and/or being used for a particular condition. At least a compatible element category may include a description identifying a compatible element as being used for a particular purpose. For example, a compatible element such as a television may be labeled with a compatible element category such as "electronic" while a compatible element such as body wash may be labeled with a compatible element category such as "health and personal care." In yet another non-limiting example, a compatible element such as a food product may be labeled with a compatible element category such as "grocery & gourmet food" while a compatible element such as hiking boots may be labeled with a compatible element category such as "outdoors." In an embodiment, a compatible element may contain a plurality of compatible element categories, for example a toaster oven may be labeled with a first compatible element category such as "electronic" and with a second compatible element category such as "kitchenware."

With continued reference to FIG. 1, at least a server 104 may be configured to select at least a compatible element by retrieving at least a compatible element similarity index value from a database and selecting at least a compatible element as a function of the compatible element similarity index value. Compatible element similarity index value as used herein, is a value assigned to a compatible element indicating a degree of similarity between a first compatible element and a second compatible element. In an embodiment, compatible element index scores may be stored in a database or datastore as described below in more detail in reference to FIG. 15. In an embodiment, a compatible element index may be calculated based on correlations between past user purchase history, past overall purchase history, and similarity of products and/or product ingredients. In an embodiment, compatible element index may be ranked whereby a high compatible element index between any two compatible elements may indicate that for any two compatible elements a large percentage of users who browsed, selected, and/or purchased a first compatible element then browsed, selected, and/or purchased a second compatible element. A low compatible element index between any two compatible elements may indicate that for any two compatible elements a small percentage of users who browsed, selected, and/or purchased a first compatible element then browsed, selected, and/or purchased a second compatible element. In an embodiment, compatible element index may be utilized to generate a compatible element index list that may be generated for a given compatible element by selecting N other compatible elements that have the highest compatible element index number and including those compatible elements on the compatible element index list. Compatible element index is described below in more detail in reference to FIG. 15.

With continued reference to FIG. 1, at least a server 104 may transmit the at least a compatible element to a user client device 156. A user client device 156 may include, without limitation, a display in communication with at least a server 104; display may include any display as described herein. A user client device 156 may include an additional computing device, such as a mobile device, laptop, desktop computer, or the like; as a non-limiting example, the user client device 156 may be a computer and/or workstation operated by a medical professional. Output may be displayed on at least a user client device 156 using an output graphical user interface, as described in more detail below. Transmission to a user client device 156 may include any of the transmission methodologies as described herein.

With continued reference to FIG. 1, at least a server 104 may include a diagnostic engine 160 operating on at least a server 104, wherein the diagnostic engine 160 may be configured to receive at least a biological extraction from a user and generate at least a diagnostic output as a function of the training data and the at least a biological extraction. At least a diagnostic output may include at least a prognostic label and at least an ameliorative process label. At least a server 104, diagnostic engine 160, and/or one or more modules operating thereon may be designed and/or configured to perform any method, method step, or sequence of method steps in any embodiment described in this disclosure, in any order and with any degree of repetition. For instance, at least a server 104 and/or diagnostic engine 160 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. At least a server 104 and/or diagnostic engine 160 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing. Diagnostic engine 160 may be configured to record at least a biological extraction from a user and generate a diagnostic output based on the at least a biological extraction. Diagnostic engine 160 is described in more detail below in reference to FIG. 2.

With continued reference to FIG. 1, system 100 may include a parsing module operating on at least a server 104. Parsing module may include any suitable hardware or software module. Parsing module may be configured to extract at least an element from at least a user activity datum wherein the at least an element further comprises at least a compatible element neutralizer and retrieve at least a datum of user fingerprint data 132 as a function of the at least an element. Compatible element neutralizer, as used herein, includes any process that may improve any physical condition identifiable in a diagnostic output. Compatible element neutralizer may include medications, supplements, nutrients, herbal remedies, exercise programs, medical procedures, physical therapies, psychological therapies and the like. In an embodiment, compatible element neutralizer may include compatible elements that may be contraindicated during the course of treatment with a particular compatible element neutralizer. For example, a compatible element neutralizer may include a specific medication designed to treat a user's nail fungus or compatible element neutralizer may include a particular supplement utilized to balance out a user's symptoms of estrogen dominance. In yet another non-limiting example, compatible element neutralizer may include treatment with a medication that contains contraindicated therapies, foods, and supplements during the course of treatment with the medication. Compatible element neutralizer may be utilized to select at least a compatible element such as when a certain medication, supplement, and/or medical procedure may be associated with a compatible element. For example, a compatible element neutralizer such as a statin medication that is utilized to reduce total cholesterol levels may be utilized to select at least a compatible element such as ubiquinol. In yet another non-limiting example, a compatible element neutralizer such as supplementation with zinc may be utilized to select at least a compatible element such as copper. In yet another non-limiting example, a compatible element neutralizer may be utilized to not select at least a compatible element. For example, a compatible element neutralizer such as doxycycline may be utilized to not select at least a compatible element containing products that may interfere with absorption of doxycycline such as magnesium, aluminum, calcium, iron, and laxatives. In an embodiment, parsing module is configured to extract at least an element from the at least a user activity datum wherein the at least an element further comprises at least a compatible element neutralizer and retrieve at least a datum of user fingerprint data as a function of the at least an element. For instance and without limitation, compatible element neutralizer may be contained within user activity datum which may be utilized to retrieve at least a datum of user fingerprint data that may be relevant during the course of treatment with compatible element neutralizer. For example, a user may have a compatible element neutralizer such as treatment with a statin medication for high cholesterol whereby consumption of grapefruit and grapefruit containing food products are contraindicated. In such an instance, parsing module may extract compatible element neutralizer from the at least a user activity datum and retrieve at least a datum of user fingerprint data relevant to user's grapefruit restriction during treatment with statin compatible element neutralizer. Such user fingerprint data may include user's browsing and/or purchasing history for compatible elements that do not include grapefruit such as a purchase of cranberry juice or orange juice. As a non-limiting example, parsing module may extract at least an element from at least a user activity datum such as a particular item or product that may be contained within at least a user activity datum. Parsing module may be configured to extract one or more words. One or more words may include without limitation, strings of one or more characters, including without limitation any sequence or sequences of letters, numbers, punctuation, diacritic marks, engineering symbols, geometric dimensioning and tolerancing (GD&T) symbols, chemical symbols and formulas, spaces, images such as emojis, whitespace, and other symbols. Textual data may be parsed into segments, which may include a simple word (sequence of letters separated by whitespace) or more generally a sequence of characters as described previously. The term segments as used herein refers to any smaller, individual groupings of text from a larger source of text; segments may be broken up by word, pair of words, sentence, or other delimitation. These segments may in turn be parsed in various ways. Textual data may be parsed into words or sequences of words, which may be considered words as well. Textual data may be parsed into "n-grams", where all sequences of n consecutive characters are considered. Any or all possible sequences of segments or words may be stored as "chains", for example for use as a Markov chain or Hidden Markov Model.

With continued reference to FIG. 1, at least a server 104 may be configured to store at least a user activity datum in the fingerprint database 128. User activity datum may be stored as any suitable data and/or data type. For instance, and without limitation, user activity datum may include textual data such as numerical, character, and/or string data. Textual data may include a standardized name and/or code. In yet another non-limiting example, user activity datum may include image data including for example an image of a user's browsing history or a photograph of a user activity datum. Images may be stored as any of the various forms as described above. Storing at least a user activity datum in the fingerprint database 128 may create a feedback mechanism that allows for fingerprint database 128 to be continuously updated with user activity datums as user activity datums are generated.

Figure 2:
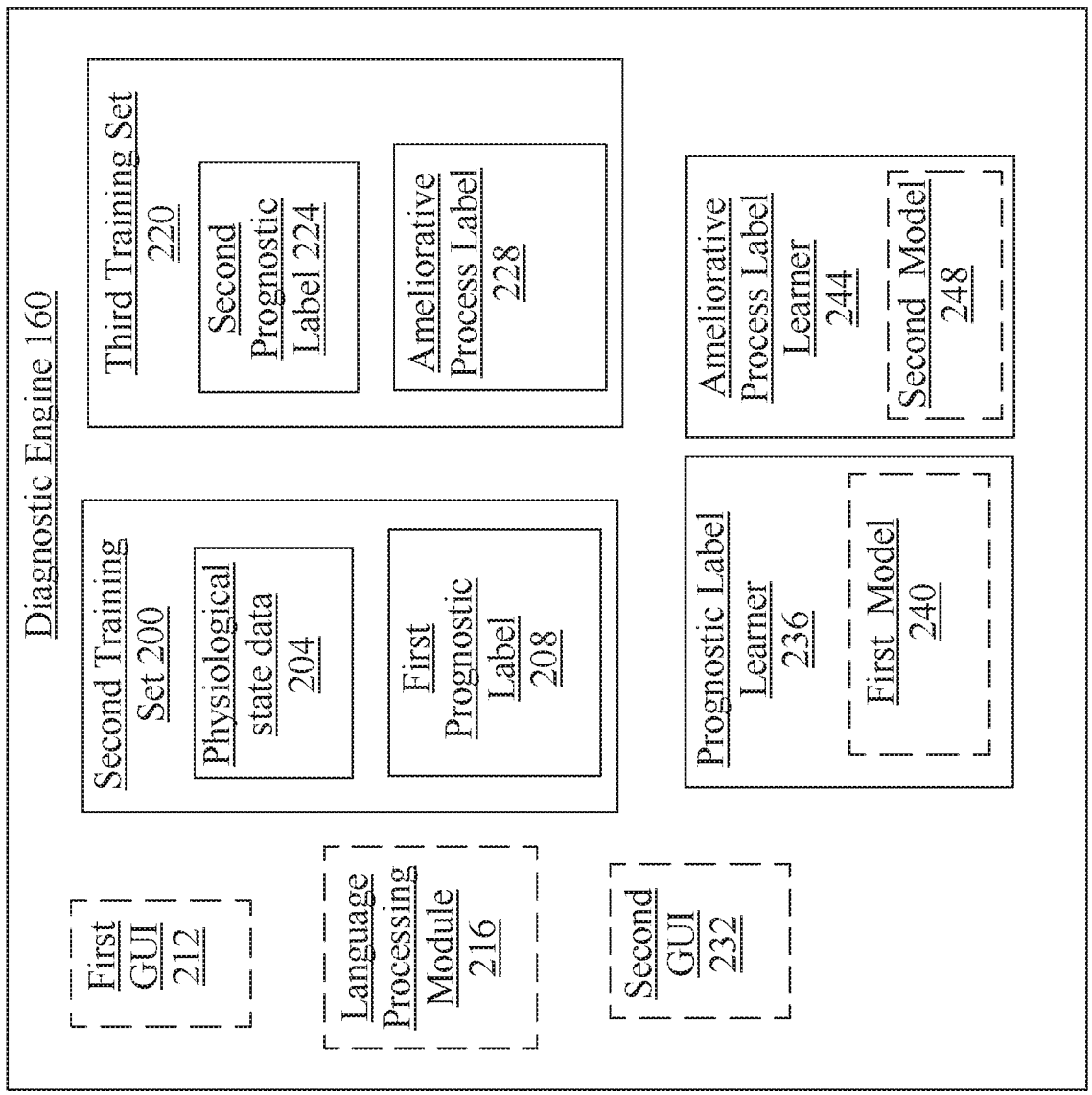
FIG. 2 is a block diagram illustrating an exemplary embodiment of a diagnostic engine.

Referring now to FIG. 2, an exemplary embodiment of diagnostic engine 160 is illustrated. In an embodiment, diagnostic engine 160 may be configured to record at least a biological extraction from a user, generate a diagnostic output based on the training data and the at least a biological extraction, and select at least a compatible element as a function of the at least a diagnostic output. At least a biological extraction may include any of the biological extractions as described above in reference to FIG. 1. In an embodiment, diagnostic engine 160 may generate a diagnostic output based on the at least a biological extraction using training data and a machine-learning model. Training data may include any of the training data as described above in reference to FIG. 1. In an embodiment, diagnostic engine 160 may receive a second training set 200 including a plurality of first data entries, each first data entry of the second training set 200 including at least an element of physiological state data 204 and at least a correlated first prognostic label 208. Physiological state data 204 may include any of the physiological state data 112 as described above in reference to FIG. 1.

Continuing to refer to FIG. 2, each element of second training set 200 includes at least a first prognostic label 208. A prognostic label, as described herein, is an element of data identifying and/or describing a current, incipient, or probable future medical condition affecting a person; medical condition may include a particular disease, one or more symptoms associated with a syndrome, a syndrome, and/or any other measure of current or future health and/or healthy aging. At least a prognostic label may be associated with a physical and/or somatic condition, a mental condition such as a mental illness, neurosis, or the like, or any other condition affecting human health that may be associated with one or more elements of physiological state data 204 as described in further detail below. Conditions associated with prognostic labels may include, without limitation one or more diseases, defined for purposes herein as conditions that negatively affect structure and/or function of part or all of an organism. Conditions associated with prognostic labels may include, without limitation, acute or chronic infections, including without limitation infections by bacteria, archaea, viruses, viroids, prions, single-celled eukaryotic organisms such as amoeba, paramecia, trypanosomes, plasmodia, leishmania, and/or fungi, and/or multicellular parasites such as nematodes, arthropods, fungi, or the like. Prognostic labels may be associated with one or more immune disorders, including without limitation immunodeficiencies and/or auto-immune conditions. Prognostic labels may be associated with one or more metabolic disorders. Prognostic labels may be associated with one or more endocrinal disorders. Prognostic labels may be associated with one or more cardiovascular disorders. Prognostic labels may be associated with one or more respiratory disorders. Prognostic labels may be associated with one or more disorders affecting connective tissue. Prognostic labels may be associated with one or more digestive disorders. Prognostic labels may be associated with one or more neurological disorders such as neuromuscular disorders, dementia, or the like. Prognostic labels may be associated with one or more disorders of the excretory system, including without limitation nephrological disorders. Prognostic labels may be associated with one or more liver disorders. Prognostic labels may be associated with one or more disorders of the bones such as osteoporosis. Prognostic labels may be associated with one or more disorders affecting joints, such as osteoarthritis, gout, and/or rheumatoid arthritis. Prognostic labels be associated with one or more cancers, including without limitation carcinomas, lymphomas, leukemias, germ cell tumor cancers, blastomas, and/or sarcomas. Prognostic labels may include descriptors of latent, dormant, and/or apparent disorders, diseases, and/or conditions. Prognostic labels may include descriptors of conditions for which a person may have a higher than average probability of development, such as a condition for which a person may have a "risk factor"; for instance, a person currently suffering from abdominal obesity may have a higher than average probability of developing type II diabetes. The above-described examples are presented for illustrative purposes only and are not intended to be exhaustive. Persons skilled in the art, upon reviewing the entirety of this disclosure, will be aware of various additional examples of conditions that may be associated with prognostic labels as described in this disclosure.

Still referring to FIG. 2, at least a prognostic label may be stored in any suitable data and/or data type. For instance, and without limitation, at least a prognostic label may include textual data, such as numerical, character, and/or string data. Textual data may include a standardized name and/or code for a disease, disorder, or the like; codes may include diagnostic codes and/or diagnosis codes, which may include without limitation codes used in diagnosis classification systems such as The International Statistical Classification of Diseases and Related Health Problems (ICD). In general, there is no limitation on forms textual data or non-textual data used as at least a prognostic label may take; persons skilled in the art, upon reviewing the entirety of this disclosure, will be aware of various forms which may be suitable for use as at least a prognostic label consistently with this disclosure.

With continued reference to FIG. 2, in each first data element of second training set 200, at least a first prognostic label 208 of the data element is correlated with at least an element of physiological state data 204 of the data element. In an embodiment, an element of physiological data is correlated with a prognostic label where the element of physiological data is located in the same data element and/or portion of data element as the prognostic label; for example, and without limitation, an element of physiological data is correlated with a prognostic element where both element of physiological data and prognostic element are contained within the same first data element of the second training set 200. As a further example, an element of physiological data is correlated with a prognostic element where both share a category label as described in further detail below, where each is within a certain distance of the other within an ordered collection of data in data element, or the like. Still further, an element of physiological data may be correlated with a prognostic label where the element of physiological data and the prognostic label share an origin, such as being data that was collected with regard to a single person or the like. In an embodiment, a first datum may be more closely correlated with a second datum in the same data element than with a third datum contained in the same data element; for instance, the first element and the second element may be closer to each other in an ordered set of data than either is to the third element, the first element and second element may be contained in the same subdivision and/or section of data while the third element is in a different subdivision and/or section of data, or the like. Persons skilled in the art, upon reviewing the entirety of this disclosure, will be aware of various forms and/or degrees of correlation between physiological data and prognostic labels that may exist in first training set 108 and/or first data element consistently with this disclosure.

In an embodiment, and still referring to FIG. 2, diagnostic engine 160 may be designed and configured to associate at least an element of physiological state data 204 with at least a category from a list of significant categories of physiological state data 204. Significant categories of physiological state data 204 may include labels and/or descriptors describing types of physiological state data 204 that are identified as being of high relevance in identifying prognostic labels. As a non-limiting example, one or more categories may identify significant categories of physiological state data 204 based on degree of diagnostic relevance to one or more impactful conditions and/or within one or more medical or public health fields. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss. As an additional example, hemoglobin levels may be useful for identifying elevated testosterone, poor oxygen deliverability, thiamin deficiency, insulin resistance, anemia, liver disease, hypothyroidism, arginine deficiency, protein deficiency, inflammation, and/or nutrient deficiencies. In a further non-limiting example, hematocrit may be useful for identifying dehydration, elevated testosterone, poor oxygen deliverability, thiamin deficiency, insulin resistance, anemia, liver disease, hypothyroidism, arginine deficiency, protein deficiency, inflammation, and/or nutrient deficiencies. Similarly, measures of lipid levels in blood, such as total cholesterol, HDL, LDL, VLDL, triglycerides, LDL-C and/or HDL-C may be recognized as useful in identifying conditions such as poor thyroid function, insulin resistance, blood glucose dysregulation, magnesium deficiency, dehydration, kidney disease, familial hypercholesterolemia, liver dysfunction, oxidative stress, inflammation, malabsorption, anemia, alcohol abuse, diabetes, hypercholesterolemia, coronary artery disease, atherosclerosis, or the like. Persons skilled in the art, upon reviewing the entirety of this disclosure, will be aware of various additional categories of physiological data that may be used consistently with this disclosure.

Still referring to FIG. 2, diagnostic engine 160 may receive the list of significant categories according to any suitable process; for instance, and without limitation, diagnostic engine 160 may receive the list of significant categories from at least an expert. In an embodiment, diagnostic engine 160 and/or a user device connected to diagnostic engine 160 may provide a graphical user interface, which may include without limitation a form or other graphical element having data entry fields, wherein one or more experts, including without limitation clinical and/or scientific experts, may enter information describing one or more categories of physiological data that the experts consider to be significant or useful for detection of conditions; fields in graphical user interface may provide options describing previously identified categories, which may include a comprehensive or near-comprehensive list of types of physiological data detectable using known or recorded testing methods, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface or the like may include fields corresponding to prognostic labels, where experts may enter data describing prognostic labels and/or categories of prognostic labels the experts consider related to entered categories of physiological data; for instance, such fields may include drop-down lists or other pre-populated data entry fields listing currently recorded prognostic labels, and which may be comprehensive, permitting each expert to select a prognostic label and/or a plurality of prognostic labels the expert believes to be predicted and/or associated with each category of physiological data selected by the expert. Fields for entry of prognostic labels and/or categories of prognostic labels may include free-form data entry fields such as text entry fields; as described above, examiners may enter data not presented in pre-populated data fields in the free-form data entry fields. Alternatively or additionally, fields for entry of prognostic labels may enable an expert to select and/or enter information describing or linked to a category of prognostic label that the expert considers significant, where significance may indicate likely impact on longevity, mortality, quality of life, or the like as described in further detail below. Graphical user interface may provide an expert with a field in which to indicate a reference to a document describing significant categories of physiological data, relationships of such categories to prognostic labels, and/or significant categories of prognostic labels. Any data described above may alternatively or additionally be received from experts similarly organized in paper form, which may be captured and entered into data in a similar way, or in a textual form such as a portable document file (PDF) with examiner entries, or the like With continued reference to FIG. 2, data information describing significant categories of physiological data, relationships of such categories to prognostic labels, and/or significant categories of prognostic labels may alternatively or additionally be extracted from one or more documents using a language processing module 216. Language processing module 216 may include any hardware and/or software module. Language processing module 216 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 2, language processing module 216 may compare extracted words to categories of physiological data recorded at diagnostic engine 160, one or more prognostic labels recorded at diagnostic engine 160, and/or one or more categories of prognostic labels recorded at diagnostic engine 160; such data for comparison may be entered on diagnostic engine 160 as described above using expert data inputs or the like. In an embodiment, one or more categories may be enumerated, to find total count of mentions in such documents. Alternatively or additionally, language processing module 216 may operate to produce a language processing model. Language processing model may include a program automatically generated by diagnostic engine 160 and/or language processing module 216 to produce associations between one or more words extracted from at least a document and detect associations, including without limitation mathematical associations, between such words, and/or associations of extracted words with categories of physiological data, relationships of such categories to prognostic labels, and/or categories of prognostic labels. Associations between language elements, where language elements include for purposes herein extracted words, categories of physiological data, relationships of such categories to prognostic labels, and/or categories of prognostic labels may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of physiological data, a given relationship of such categories to prognostic labels, and/or a given category of prognostic labels. As a further example, statistical correlations and/or mathematical associations may include probabilistic formulas or relationships indicating a positive and/or negative association between at least an extracted word and/or a given category of physiological data, a given relationship of such categories to prognostic labels, and/or a given category of prognostic labels; positive or negative indication may include an indication that a given document is or is not indicating a category of physiological data, relationship of such category to prognostic labels, and/or category of prognostic labels is or is not significant. For instance, and without limitation, a negative indication may be determined from a phrase such as "telomere length was not found to be an accurate predictor of overall longevity," whereas a positive indication may be determined from a phrase such as "telomere length was found to be an accurate predictor of dementia," as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at diagnostic engine 160, or the like.

Still referring to FIG. 2, language processing module 216 and/or diagnostic engine 160 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs has used herein are statistical models with inference algorithms that that may be applied to the models. In such models, a hidden state to be estimated may include an association between an extracted word category of physiological data, a given relationship of such categories to prognostic labels, and/or a given category of prognostic labels. There may be a finite number of category of physiological data, a given relationship of such categories to prognostic labels, and/or a given category of prognostic labels to which an extracted word may pertain; an HMM inference algorithm, such as the forward-backward algorithm or the Viterbi algorithm, may be used to estimate the most likely discrete state given a word or sequence of words. Language processing module 216 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

With continued reference to FIG. 2, at least a server 104 and/or diagnostic engine 160 may be configured to receive a second training set including a plurality of second data entries. Each second data entry of the second training set may include at least a compatible label 116 and at least a correlated compatible category label. Correlation may include any correlation suitable of at least an element of physiological state data 112 and at least a correlated compatible label 116 as described above. As used herein, a compatible category label is a classifier which identifies compatible products and/or ingredients having particular shared characteristics. Shared characteristics may include traits and/or qualities that identify a product and/or ingredient as being used for a particular purpose and/or suitable for a particular condition. For example, products free of gluten and dairy may contain a compatible category label as indicating products free of gluten and dairy. In yet another non-limiting example, a product such as organic toothpaste that doesn't contain any preservatives or heavy metals and is sourced only from plants may contain a compatible category label as indicating being suitable for use by those most at risk for heavy metal toxicity including persons with mercury dental fillings, smokers, and users with chronic autoimmune conditions. Training data may be sorted or filtered according to "categories" or "significance scores" such as by trimming training data to categories that are most significant and/or most closely related to a given user's categories. In an embodiment, training data may be sorted according to domain limitations. Expert input or other input of "categories" may create training data entries where "categories" are a kind of label and associations between them are used to create correlations. "Categories" discovered or defined by any process may become labels of the sorts of things they are related to, in the training data. Training data may be received, a category may be associated with it to create a first kind of label, and a second category may be associated with it to create a second kind of label, thereby creating a training data entry. Unsupervised machine learning identification of associations may also create training data by creating new categories and creating data entries associating them to each other. Unsupervised machine-learning identification of associations may create training data by making new categories and allowing experts to identify associations or making new categories and obtaining associations from documents linking two newly derived categories together. Outputs of each machine-learning process may have associated "categories" and may be sorted or filtered according to "categories" including prior to use as inputs to subsequent processes.

With continued reference to FIG. 2, at least a server 104 and/or diagnostic engine 160 may be configured to receive component elements of training sets and utilize components to generate machine-learning models to select at least a compatible element. Components may include any of the data sets described in first training set, second training set, and third training set. For example, at least a server may receive components and relate elements between first prognostic label 208 and compatible label or compatible category labels using machine-learning models as described herein. In yet another non-limiting example, at least a server 104 and/or diagnostic engine 160 may relate elements between ameliorative process label 228 and compatible label or ameliorative process label 228 and compatible category labels. In yet another non-limiting example, at least a server 104 and/or diagnostic engine 160 may relate elements between diagnostic outputs and compatible label or diagnostic output and compatible category labels.

Continuing to refer to FIG. 2, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 2, language processing module 216 may use a corpus of documents to generate associations between language elements in a language processing module 216, and diagnostic engine 160 may then use such associations to analyze words extracted from one or more documents and determine that the one or more documents indicate significance of a category of physiological data, a given relationship of such categories to prognostic labels, and/or a given category of prognostic labels. In an embodiment, diagnostic engine 160 may perform this analysis using a selected set of significant documents, such as documents identified by one or more experts as representing good science, good clinical analysis, or the like; experts may identify or enter such documents via graphical user interface as described above in reference to FIG. 9, or may communicate identities of significant documents according to any other suitable method of electronic communication, or by providing such identity to other persons who may enter such identifications into diagnostic engine 160. Documents may be entered into diagnostic engine 160 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, diagnostic engine 160 may automatically obtain the document using such an identifier, for instance by submitting a request to a database or compendium of documents such as JSTOR as provided by Ithaka Harbors, Inc. of New York.

Continuing to refer to FIG. 2, whether an entry indicating significance of a category of physiological data, a given relationship of such categories to prognostic labels, and/or a given category of prognostic labels is entered via graphical user interface, alternative submission means, and/or extracted from a document or body of documents as described above, an entry or entries may be aggregated to indicate an overall degree of significance. For instance, each category of physiological data, relationship of such categories to prognostic labels, and/or category of prognostic labels may be given an overall significance score; overall significance score may, for instance, be incremented each time an expert submission and/or paper indicates significance as described above. Persons skilled in the art, upon reviewing the entirety of this disclosure will be aware of other ways in which scores may be generated using a plurality of entries, including averaging, weighted averaging, normalization, and the like. Significance scores may be ranked; that is, all categories of physiological data, relationships of such categories to prognostic labels, and/or categories of prognostic labels may be ranked according significance scores, for instance by ranking categories of physiological data, relationships of such categories to prognostic labels, and/or categories of prognostic labels higher according to higher significance scores and lower according to lower significance scores. Categories of physiological data, relationships of such categories to prognostic labels, and/or categories of prognostic labels may be eliminated from current use if they fail a threshold comparison, which may include a comparison of significance score to a threshold number, a requirement that significance score belong to a given portion of ranking such as a threshold percentile, quartile, or number of top-ranked scores. Significance scores may be used to filter outputs as described in further detail below; for instance, where a number of outputs are generated and automated selection of a smaller number of outputs is desired, outputs corresponding to higher significance scores may be identified as more probable and/or selected for presentation while other outputs corresponding to lower significance scores may be eliminated. Alternatively or additionally, significance scores may be calculated per sample type; for instance, entries by experts, documents, and/or descriptions of purposes of a given type of physiological test or sample collection as described above may indicate that for that type of physiological test or sample collection a first category of physiological data, relationship of such category to prognostic labels, and/or category of prognostic labels is significant with regard to that test, while a second category of physiological data, relationship of such category to prognostic labels, and/or category of prognostic labels is not significant; such indications may be used to perform a significance score for each category of physiological data, relationship of such category to prognostic labels, and/or category of prognostic labels is or is not significant per type of biological extraction, which then may be subjected to ranking, comparison to thresholds and/or elimination as described above.

Still referring to FIG. 2, diagnostic engine 160 may detect further significant categories of physiological data, relationships of such categories to prognostic labels, and/or categories of prognostic labels using machine-learning processes, including without limitation unsupervised machine-learning processes as described in further detail below; such newly identified categories, as well as categories entered by experts in free-form fields as described above, may be added to pre-populated lists of categories, lists used to identify language elements for language learning module, and/or lists used to identify and/or score categories detected in documents, as described above.

Continuing to refer to FIG. 2, in an embodiment, diagnostic engine 160 may be configured, for instance as part of receiving the second training set 200, to associate at least correlated first prognostic label 208 with at least a category from a list of significant categories of prognostic labels. Significant categories of prognostic labels may be acquired, determined, and/or ranked as described above. As a non-limiting example, prognostic labels may be organized according to relevance to and/or association with a list of significant conditions. A list of significant conditions may include, without limitation, conditions having generally acknowledged impact on longevity and/or quality of life; this may be determined, as a non-limiting example, by a product of relative frequency of a condition within the population with years of life and/or years of able-bodied existence lost, on average, as a result of the condition. A list of conditions may be modified for a given person to reflect a family history of the person; for instance, a person with a significant family history of a particular condition or set of conditions, or a genetic profile having a similarly significant association therewith, may have a higher probability of developing such conditions than a typical person from the general population, and as a result diagnostic engine 160 may modify list of significant categories to reflect this difference.

Still referring to FIG. 2, diagnostic engine 160 is designed and configured to receive a third training set 220 including a plurality of second data entries. Each second data entry of the third training set 220 includes at least a second prognostic label 224; at least a second prognostic label 224 may include any label suitable for use as at least a first prognostic label 208 as described above. Each second data entry of the third training set 220 includes at least an ameliorative process label 228 correlated with the at least a second prognostic label 224, where correlation may include any correlation suitable for correlation of at least a first prognostic label 208 to at least an element of physiological data as described above. As used herein, an ameliorative process label 228 is an identifier, which may include any form of identifier suitable for use as a prognostic label as described above, identifying a process that tends to improve a physical condition of a user, where a physical condition of a user may include, without limitation, any physical condition identifiable using a prognostic label. Ameliorative processes may include, without limitation, exercise programs, including amount, intensity, and/or types of exercise recommended. Ameliorative processes may include, without limitation, dietary or nutritional recommendations based on data including nutritional content, digestibility, or the like. Ameliorative processes may include one or more medical procedures. Ameliorative processes may include one or more physical, psychological, or other therapies. Ameliorative processes may include one or more medications. Persons skilled in the art, upon reviewing the entirety of this disclosure, will be aware of various processes that may be used as ameliorative processes consistently with this disclosure.

Continuing to refer to FIG. 2, in an embodiment diagnostic engine 160 may be configured, for instance as part of receiving third training set 220, to associate the at least second prognostic label 224 with at least a category from a list of significant categories of prognostic labels. This may be performed as described above for use of lists of significant categories with regard to at least a first prognostic label 208. Significance may be determined, and/or association with at least a category, may be performed for prognostic labels in first training set 108 according to a first process as described above and for prognostic labels in third training set 220 according to a second process as described above.

Still referring to FIG. 2, diagnostic engine 160 may be configured, for instance as part of receiving third training set 220, to associate at least a correlated ameliorative process label 228 with at least a category from a list of significant categories of ameliorative process labels 228. In an embodiment, diagnostic engine 160 and/or a user device connected to diagnostic engine 160 may provide a second graphical user interface 232 which may include without limitation a form or other graphical element having data entry fields, wherein one or more experts, including without limitation clinical and/or scientific experts, may enter information describing one or more categories of prognostic labels that the experts consider to be significant as described above; fields in graphical user interface may provide options describing previously identified categories, which may include a comprehensive or near-comprehensive list of types of prognostic labels, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface or the like may include fields corresponding to ameliorative labels, where experts may enter data describing ameliorative labels and/or categories of ameliorative labels the experts consider related to entered categories of prognostic labels; for instance, such fields may include drop-down lists or other pre-populated data entry fields listing currently recorded ameliorative labels, and which may be comprehensive, permitting each expert to select an ameliorative label and/or a plurality of ameliorative labels the expert believes to be predicted and/or associated with each category of prognostic labels selected by the expert. Fields for entry of ameliorative labels and/or categories of ameliorative labels may include free-form data entry fields such as text entry fields; as described above, examiners may enter data not presented in pre-populated data fields in the free-form data entry fields. Alternatively or additionally, fields for entry of ameliorative labels may enable an expert to select and/or enter information describing or linked to a category of ameliorative label that the expert considers significant, where significance may indicate likely impact on longevity, mortality, quality of life, or the like as described in further detail below. Graphical user interface may provide an expert with a field in which to indicate a reference to a document describing significant categories of prognostic labels, relationships of such categories to ameliorative labels, and/or significant categories of ameliorative labels. Such information may alternatively be entered according to any other suitable means for entry of expert data as described above. Data concerning significant categories of prognostic labels, relationships of such categories to ameliorative labels, and/or significant categories of ameliorative labels may be entered using analysis of documents using language processing module 216 or the like as described above.

In an embodiment, and still referring to FIG. 2, diagnostic engine 160 may extract at least a second data entry from one or more documents; extraction may be performed using any language processing method as described above. Diagnostic engine 160 may be configured, for instance as part of receiving third training set 220, to receive at least a document describing at least a medical history and extract at least a second data entry of plurality of second data entries from the at least a document. A medical history document may include, for instance, a document received from an expert and/or medical practitioner describing treatment of a patient; document may be anonymized by removal of one or more patient-identifying features from document. A medical history document may include a case study, such as a case study published in a medical journal or written up by an expert. A medical history document may contain data describing and/or described by a prognostic label; for instance, the medical history document may list a diagnosis that a medical practitioner made concerning the patient, a finding that the patient is at risk for a given condition and/or evinces some precursor state for the condition, or the like. A medical history document may contain data describing and/or described by an ameliorative process label 228; for instance, the medical history document may list a therapy, recommendation, or other ameliorative process that a medical practitioner described or recommended to a patient. A medical history document may describe an outcome; for instance, medical history document may describe an improvement in a condition describing or described by a prognostic label, and/or may describe that the condition did not improve. Prognostic labels, ameliorative process labels 228, and/or efficacy of ameliorative process labels 228 may be extracted from and/or determined from one or more medical history documents using any processes for language processing as described above; for instance, language processing module 216 may perform such processes. As a non-limiting example, positive and/or negative indications regarding ameliorative processes identified in medical history documents may be determined in a manner described above for determination of positive and/or negative indications regarding categories of physiological data, relationships of such categories to prognostic labels, and/or categories of prognostic labels.

With continued reference to FIG. 2, diagnostic engine 160 may be configured, for instance as part of receiving third training set 220, to receiving at least a second data entry of the plurality of second data entries from at least an expert. This may be performed, without limitation using second graphical user interface 148 as described above.

With continued reference to FIG. 2, diagnostic engine 160 may include a prognostic label learner 236 operating on the diagnostic engine 160, the prognostic label learner 236 designed and configured to generate the at least a prognostic output as a function of the second training set 200 and the at least a biological extraction. Prognostic label learner 236 may include any hardware and/or software module. Prognostic label learner 236 is designed and configured to generate outputs using machine learning processes. A machine learning process is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language.

Still referring to FIG. 2, prognostic label learner 236 may be designed and configured to generate at least a prognostic output by creating at least a first machine-learning model 240 relating physiological state data 204 to prognostic labels using the second training set 200 and generating the at least a prognostic output using the first machine-learning model 240; at least a first machine-learning model 240 may include one or more models that determine a mathematical relationship between physiological state data 204 and prognostic labels. Such models may include without limitation model developed using linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithm used to generate first machine-learning model 240 may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 2, prognostic label learner 236 may generate prognostic output using alternatively or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using second training set 200; the trained network may then be used to apply detected relationships between elements of physiological state data 204 and prognostic labels.

Figure 3:
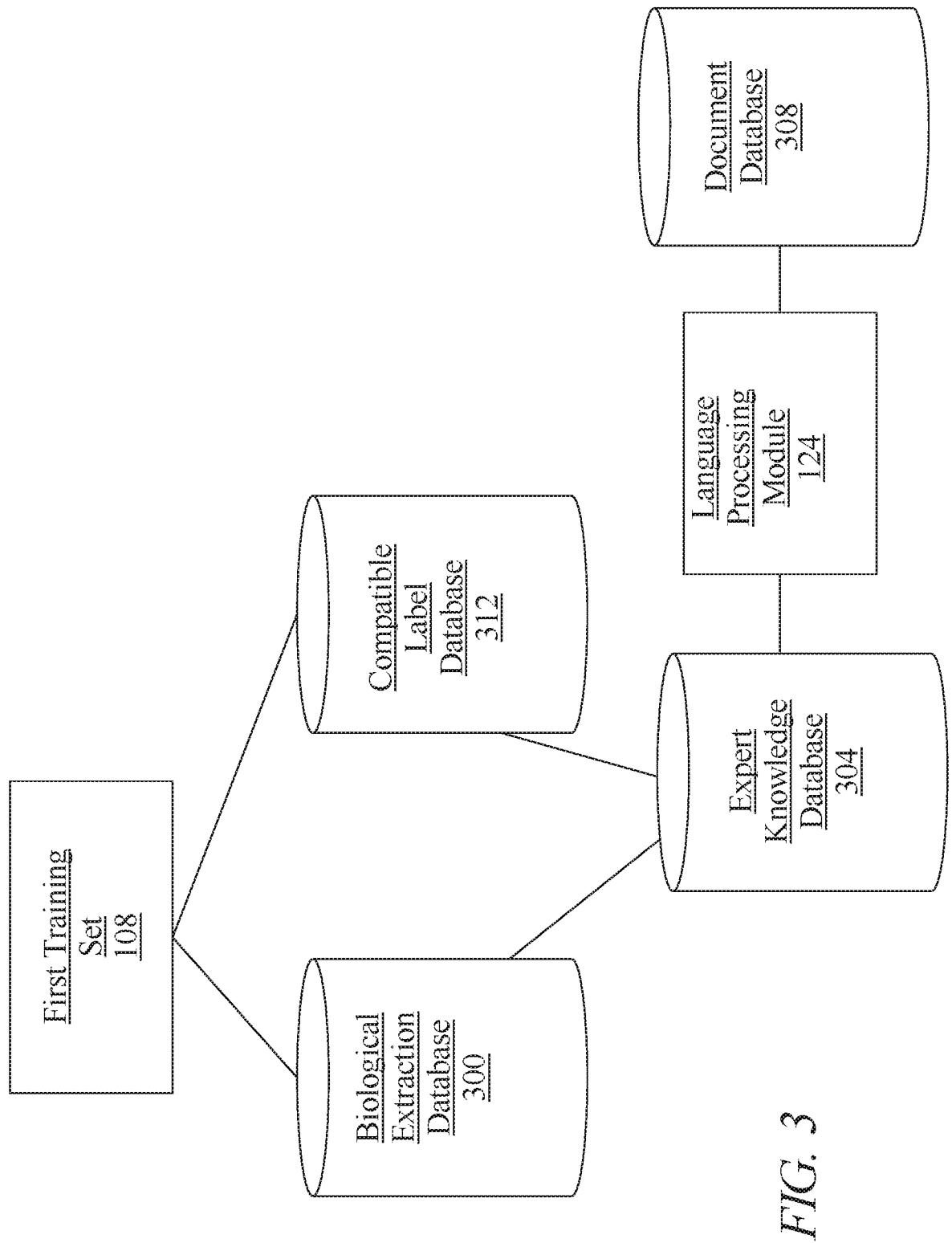
FIG. 3 is a block diagram illustrating embodiments of data storage facilities for use in disclosed systems and methods.

Referring now to FIG. 3, data incorporated in first training set may be incorporated in one or more databases. As a non-limiting example, one or elements of physiological data may be stored in and/or retrieved from a biological extraction database 300. A biological extraction database 300 may include any data structure for ordered storage and retrieval of data, which may be implemented as a hardware or software module. A biological extraction database 300 may be implemented, without limitation, as a relational database, a key-value retrieval datastore such as a NOSQL database, or any other format or structure for use as a datastore that a person skilled in the art would recognize as suitable upon review of the entirety of this disclosure. A biological extraction database 300 may include a plurality of data entries and/or records corresponding to elements of physiological data as described above. Data entries and/or records may describe, without limitation, data concerning particular biological extractions that have been collected; entries may describe reasons for collection of samples, such as without limitation one or more conditions being tested for, which may be listed with related compatible label. Data entries may include compatible label and/or other descriptive entries describing results of evaluation of past biological extractions, including diagnoses that were associated with such samples, prognoses and/or conclusions regarding likelihood of future diagnoses that were associated with such samples, and/or other medical or diagnostic conclusions that were derived. Such conclusions may have been generated by diagnostic engine 160 128 in previous iterations of methods, with or without validation of correctness by medical professionals. Data entries in a biological extraction database 300 may be flagged with or linked to one or more additional elements of information, which may be reflected in data entry cells and/or in linked tables such as tables related by one or more indices in a relational database; one or more additional elements of information may include data associating a biological extraction and/or a person from whom a biological extraction was extracted or received with one or more cohorts, including demographic groupings such as ethnicity, sex, age, income, geographical region, or the like, one or more common diagnoses or physiological attributes shared with other persons having biological extractions reflected in other data entries, or the like. Additional elements of information may include one or more categories of physiological data as described above. Additional elements of information may include descriptions of particular methods used to obtain biological extractions, such as without limitation physical extraction of blood samples or the like, capture of data with one or more sensors, and/or any other information concerning provenance and/or history of data acquisition. Persons skilled in the art, upon reviewing the entirety of this disclosure, will be aware of various ways in which data entries in a biological extraction database 300 may reflect categories, cohorts, and/or populations of data consistently with this disclosure.

With continued reference to FIG. 3, at least a server 104 and/or another device in communication with at least a server 104 may populate one or more fields in biological extraction database 300 using expert information, which may be extracted or retrieved from an expert knowledge database 304. An expert knowledge database 304 may include any data structure and/or data store suitable for use as a biological extraction database 300 as described above. Expert knowledge database 304 may include data entries reflecting one or more expert submissions of data such as may have been submitted according to any process described above in reference to FIGS. 1-2 including without limitation by using graphical user interface 120 and/or second graphical user interface 148. Expert knowledge database may include one or more fields generated by language processing module, such as without limitation fields extracted from one or more documents as described above. For instance, and without limitation, one or more categories of physiological data and/or related compatible label and/or categories of compatible label associated with an element of physiological state data 112 as described above may be stored in generalized from in an expert knowledge database 304 and linked to, entered in, or associated with entries in a biological extraction database 300. Documents may be stored and/or retrieved by at least a server 104 and/or language processing module in and/or from a document database 308; document database 308 may include any data structure and/or data store suitable for use as biological extraction database 300 as described above.

Documents in document database 308 may be linked to and/or retrieved using document identifiers such as URI and/or URL data, citation data, or the like; persons skilled in the art, upon reviewing the entirety of this disclosure, will be aware of various ways in which documents may be indexed and retrieved according to citation, subject matter, author, date, or the like as consistent with this disclosure.

With continued reference to FIG. 3, a compatible label database 312, which may be implemented in any manner suitable for implementation of biological extraction database 300, may be used to store compatible labels used by at least a server 104, including any compatible label correlated with elements of physiological data in first training set 108 as described above; compatible label may be linked to or refer to entries in biological extraction database 300 to which compatible label correspond. Linking may be performed by reference to historical data concerning biological extractions, such as diagnoses, prognoses, and/or other medical conclusions derived from biological extractions in the past; alternatively or additionally, a relationship between a compatible label and a data entry in biological extraction database 300 may be determined by reference to a record in an expert knowledge database 304 linking a given compatible label to a given category of biological extraction as described above. Entries in compatible label database 312 may be associated with one or more categories of compatible label as described above, for instance using data stored in and/or extracted from an expert knowledge database 304.

With continued reference to FIG. 3, first training set 108 may be populated by retrieval of one or more records from biological extraction database 300 and/or compatible label database 312; in an embodiment, entries retrieved from biological extraction database 300 and/or compatible label database 312 may be filtered and or select via query to match one or more additional elements of information as described above, so as to retrieve a first training set 108 including data belonging to a given cohort, demographic population, or other set, so as to generate outputs as described below that are tailored to a person or persons with regard to whom at least a server 104 classifies biological extractions to compatible label as set forth in further detail below. Persons skilled in the art, upon reviewing the entirety of this disclosure, will be aware of various ways in which records may be retrieved from biological extraction database 300 and/or compatible label database to generate a first training set 108 to reflect individualized group data pertaining to a person of interest in operation of system and/or method, including without limitation a person with regard to whom at least a biological extraction is being evaluated as described in further detail below. At least a server 104 may alternatively or additionally receive a first training set 108 and store one or more entries in biological extraction database 300 and/or compatible label database 312 as extracted from elements of first training set.

Figure 4:
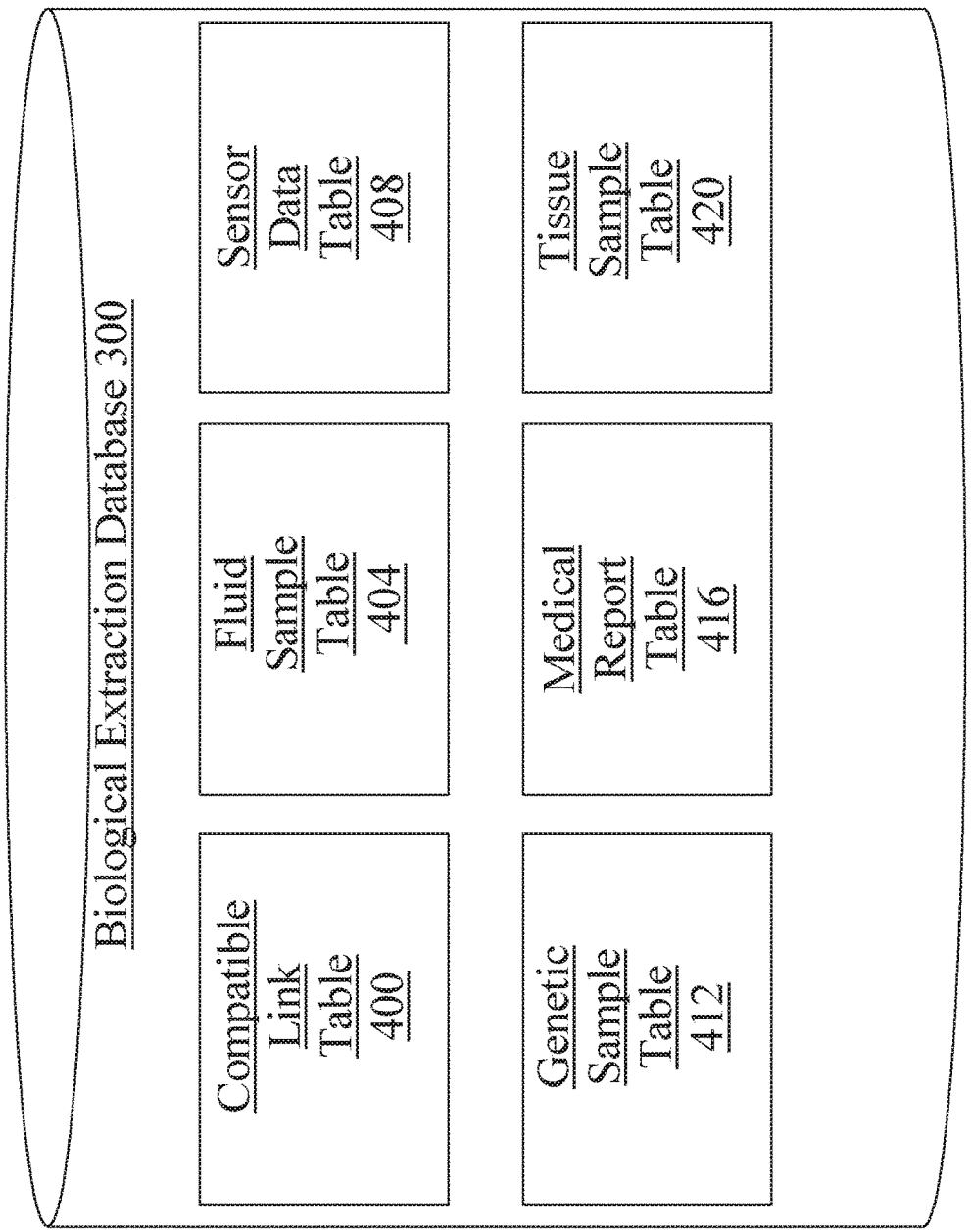
FIG. 4 is a block diagram illustrating an exemplary embodiment of a biological extraction database.

Referring now to FIG. 4, one or more database tables in biological extraction database 300 may include, as a non-limiting example, n compatible link table 400. Compatible link table 400 may be a table relating biological extraction data as described above to compatible label; for instance, where an expert has entered data relating a compatible label to a category of biological extraction data and/or to an element of biological extraction data via first graphical user interface as described above, one or more rows recording such an entry may be inserted in compatible link table 400. Alternatively or additionally, linking of compatible label to biological extraction data may be performed entirely in compatible label database as described below.

With continued reference to FIG. 4, biological extraction database 300 may include tables listing one or more samples according to sample source. For instance, and without limitation, biological extraction database 300 may include a fluid sample table 404 listing samples acquired from a person by extraction of fluids, such as without limitation blood, lymph cerebrospinal fluid, or the like. As another non-limiting example, biological extraction database 300 may include a sensor data table 408, which may list samples acquired using one or more sensors, for instance as described in further detail below. As a further non-limiting example, biological extraction database 300 may include a genetic sample table 412, which may list partial or entire sequences of genetic material. Genetic material may be extracted and amplified, as a non-limiting example, using polymerase chain reactions (PCR) or the like. As a further example, also non-limiting, biological extraction database 300 may include a medical report table 416, which may list textual descriptions of medical tests, including without limitation radiological tests or tests of strength and/or dexterity or the like. Data in medical report table may be sorted and/or categorized using a language processing module, for instance, translating a textual description into a numerical value and a label corresponding to a category of physiological data; this may be performed using any language processing algorithm or algorithms as referred to in this disclosure. As another non-limiting example, biological extraction database 300 may include a tissue sample table 420, which may record biological extractions obtained using tissue samples. Tables presented above are presented for exemplary purposes only; persons skilled in the art will be aware of various ways in which data may be organized in biological extraction database 300 consistently with this disclosure.

Figure 5:
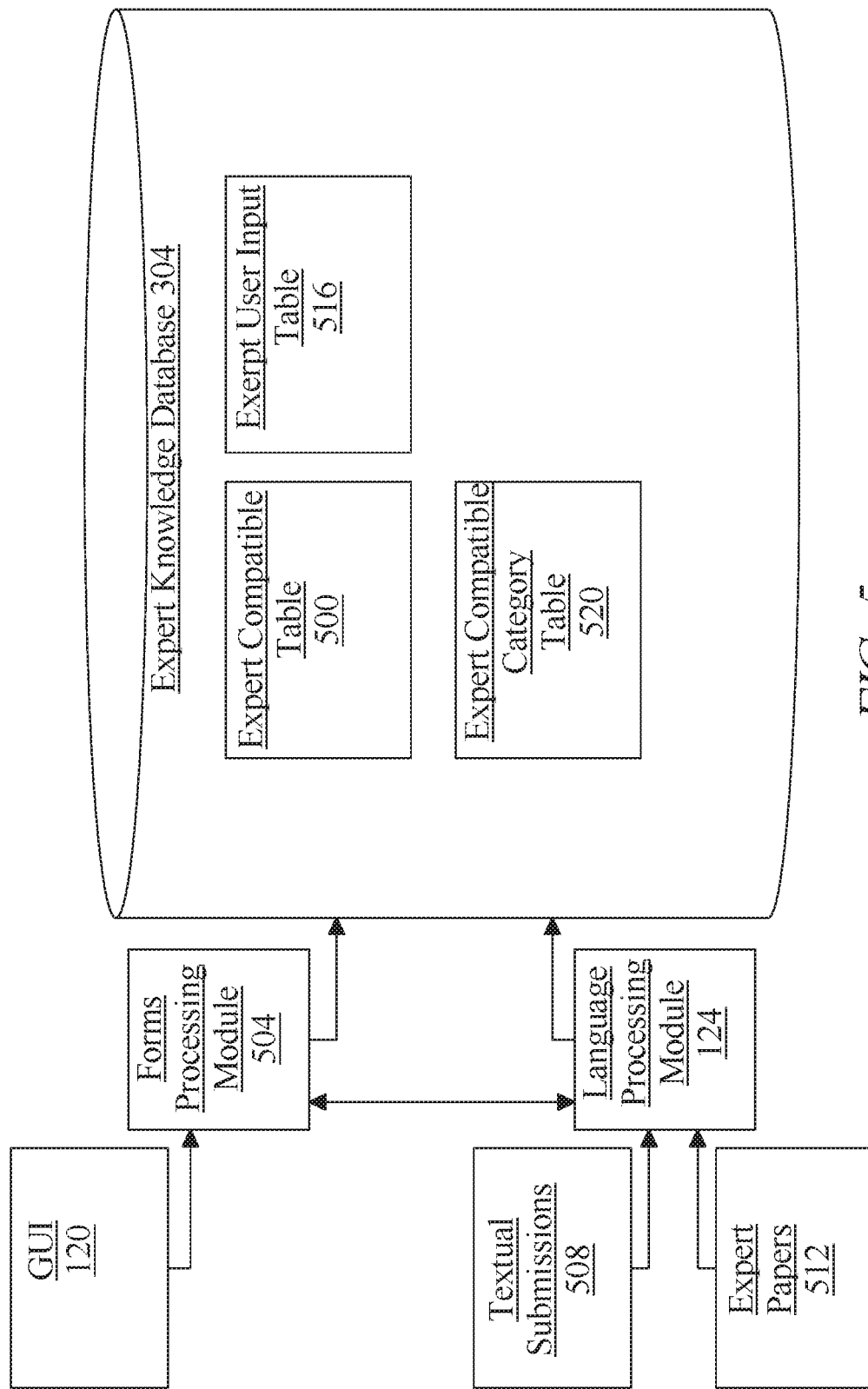
FIG. 5 is a block diagram illustrating an exemplary embodiment of an expert knowledge database.

Referring now to FIG. 5, an exemplary embodiment of an expert knowledge database 304 is illustrated. Expert knowledge database 304 may, as a non-limiting example, organize data stored in the expert knowledge database 304 according to one or more database tables. One or more database tables may be linked to one another by, for instance, common column values. For instance, a common column between two tables of expert knowledge database 304 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 5, one or more database tables in expert knowledge database 304 may include, as a non-limiting example, an expert compatible table 500. Expert compatible table 500 may be a table relating biological extraction data as described above to compatible label; for instance, where an expert has entered data relating a compatible label to a category of biological extraction data and/or to an element of biological extraction data via graphical user interface 120 as described above, one or more rows recording such an entry may be inserted in expert compatible table 500. In an embodiment, a forms processing module 504 may sort data entered in a submission via graphical user interface 120 by, for instance, sorting data from entries in the graphical user interface 120 to related categories of data; for instance, data entered in an entry relating in the graphical user interface 120 to a compatible label may be sorted into variables and/or data structures for storage of compatible label, while data entered in an entry relating to a category of physiological data and/or an element thereof may be sorted into variables and/or data structures for the storage of, respectively, categories of physiological data or elements of physiological data. Where data is chosen by an expert from pre-selected entries such as drop-down lists, data may be stored directly; where data is entered in textual form, language processing module 124 may be used to map data to an appropriate existing label, for instance using a vector similarity test or other synonym-sensitive language processing test to map physiological data to an existing label. Alternatively or additionally, when a language processing algorithm, such as vector similarity comparison, indicates that an entry is not a synonym of an existing label, language processing module 124 may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 508, such as accomplished by filling out a paper or PDF form and/or submitting narrative information, may likewise be processed using language processing module 124. Data may be extracted from expert papers 512, which may include without limitation publications in medical and/or scientific journals, by language processing module 124 via any suitable process as described herein. Persons skilled in the art, upon reviewing the entirety of this disclosure, will be aware of various additional methods whereby novel terms may be separated from already-classified terms and/or synonyms therefore, as consistent with this disclosure. Expert compatible table 500 may include a single table and/or a plurality of tables; plurality of tables may include tables for particular categories of compatible label such as books, beauty, electronics, health and personal care, home and garden, outdoors, (not shown), to name a few non-limiting examples presented for illustrative purposes only.

With continued reference to FIG. 5, one or more database tables in expert knowledge database 304 may include, an expert user input table 516, expert data populating such tables may be provided, without limitation, using any process described above, including entry of data from graphical user interface 120 via forms processing module 504 and/or language processing module 124, processing of textual submissions 508, or processing of expert papers 512. For instance, and without limitation, an expert user input table 516 may list one or categories of user input processes, and/or links of such one or more user inputs processes to compatible labels, as provided by experts according to any method of processing and/or entering expert data as described above. As a further example an expert compatible category table 520 may list one or more expert compatible categories based on compatible labels and/or biological extractions, including for example a compatible category table for skin care suitable for use by users who have diabetes, a compatible category table for clothing suitable for use by users who have diabetes, and a compatible category table for sporting goods suitable for use by users who have rheumatoid arthritis as provided by experts according to any method of processing and/or entering expert data as described above. Tables presented above are presented for exemplary purposes only; persons skilled in the art will be aware of various ways in which data may be organized in expert knowledge database 304.

Figure 6:
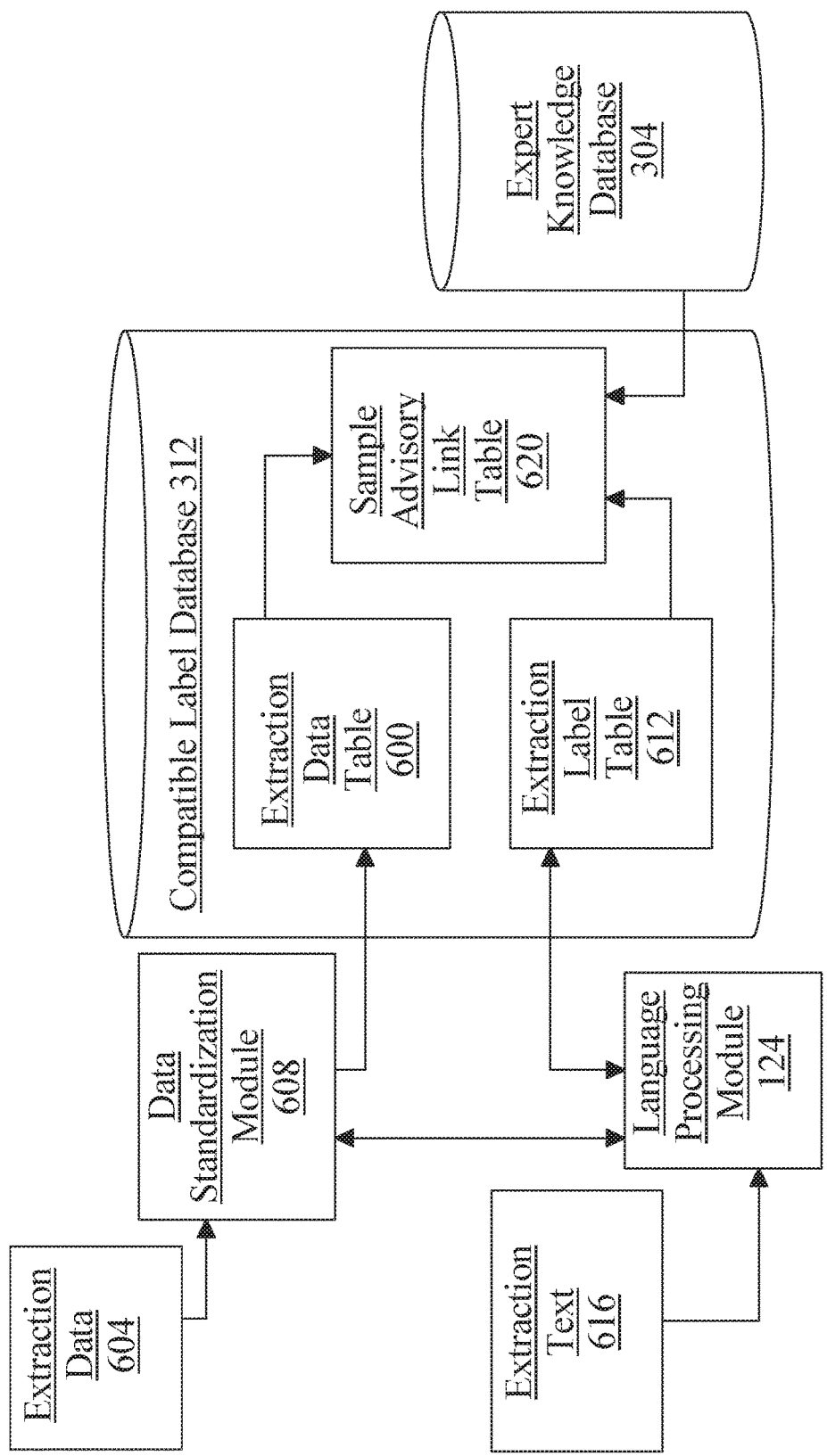
FIG. 6 is a block diagram illustrating an exemplary embodiment of a compatible label database.

Referring now to FIG. 6, an exemplary embodiment of compatible label database 312 is illustrated. Compatible label database 312 may, as a non-limiting example, organize data stored in the compatible label database 312 according to one or more database tables. One or more database tables may be linked to one another by, for instance, common column values. For instance, a common column between two tables of compatible label database 312 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 6, one or more database tables in compatible label database 312 may include, as a non-limiting example, an extraction data table 600. Extraction data table 600 may be a table listing sample data, along with, for instance, one or more linking columns to link such data to other information stored in compatible label database 312. In an embodiment, extraction data 604 may be acquired, for instance from biological extraction database 300, in a raw or unsorted form, and may be translated into standard forms, such as standard units of measurement, labels associated with particular physiological data values, or the like; this may be accomplished using a data standardization module 608, which may perform unit conversions. Data standardization module 608 may alternatively or additionally map textual information, such as labels describing values tested for or the like, using language processing module 124 or equivalent components and/or algorithms thereto.

Continuing to refer to FIG. 6, compatible label database 312 may include an extraction label table 612; extraction label table 612 may list compatible label 116 received with and/or extracted from biological extractions, for instance as received in the form of extraction text 616. A language processing module 124 may compare textual information so received to compatible label 116 and/or from new compatible label 116 according to any suitable process as described above. Extraction advisory link table 620 may combine extractions with compatible label 116, as acquired from extraction label table and/or expert knowledge database 304; combination may be performed by listing together in rows or by relating indices or common columns of two or more tables to each other. Tables presented above are presented for exemplary purposes only; persons skilled in the art will be aware of various ways in which data may be organized in expert knowledge database 304 consistently with this disclosure.

Figure 7:
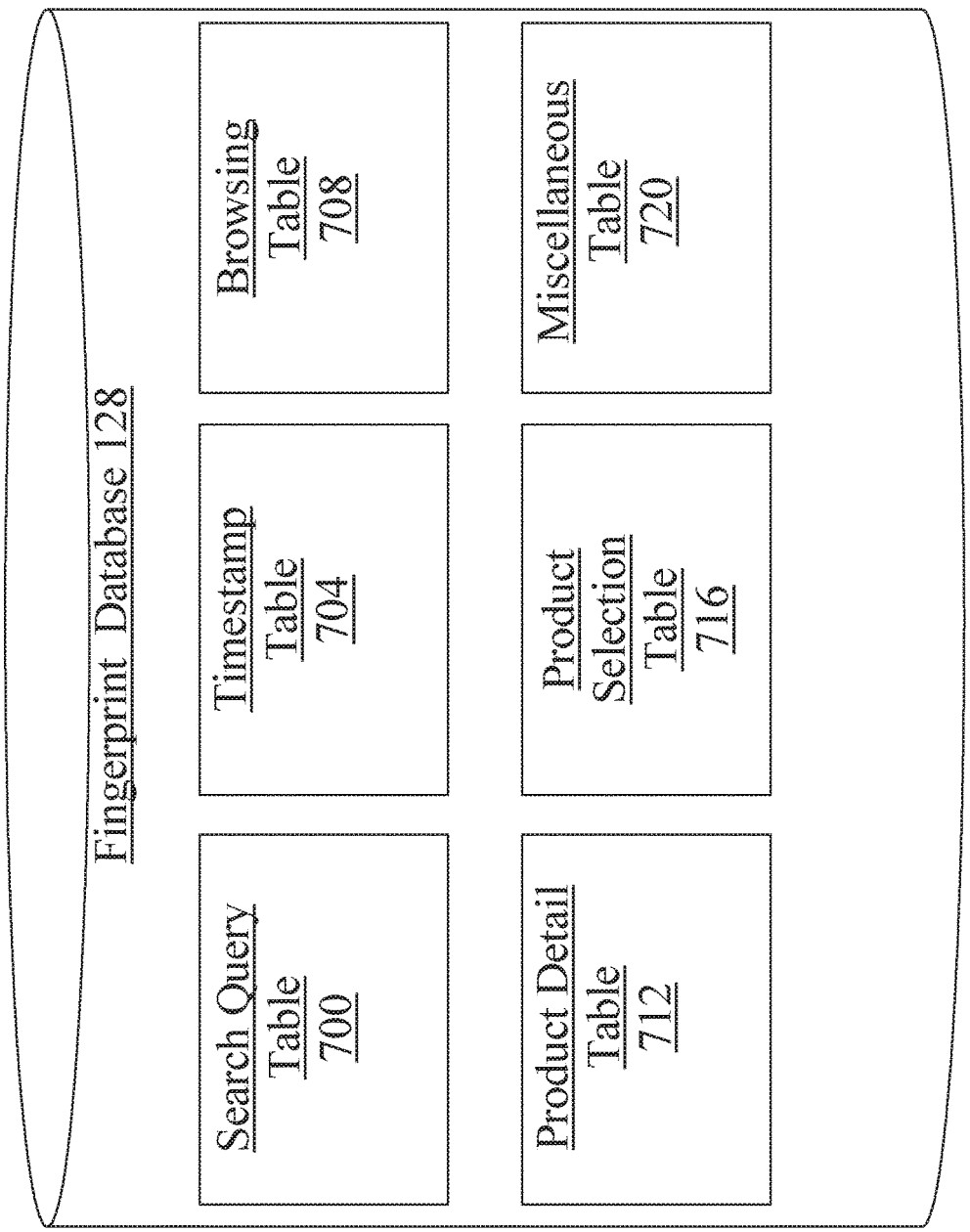
FIG. 7 is a block diagram illustrating an exemplary embodiment of a fingerprint database.

Referring now to FIG. 7, an exemplary embodiment of fingerprint database 128 is illustrated, which may be implemented in any manner suitable for implementation of biological extraction database 300. Fingerprint database 128 may include user fingerprint information including any of the fingerprint data 132 as described above in reference to FIG. 1. One or more database tables in fingerprint database 128 may include, without limitation a search query table 700; search query table 700 may include information describing one or more search queries and/or search query actions that a user entered within system 100. One or more search queries may include any data and/or information describing any previous search queries that a user entered. For example, search query table 700 may include information describing a particular product and/or item that a user generated a search query for such as a food product such as coffee or a cleaning product such as dish soap. Search query actions may include any action performed by a user in relation to a query. Search query actions may include for example, a reformulation of a search query, a term swap, a term addition, a term addition, an abandonment of the search query, a refinement of the search query, a scope change of the search query and the like. For example, search query table 700 may include data describing a user who refines a search query from "kitchen utensil" to "metal spatula." One or more database tables in fingerprint database 128 may include, without limitation a timestamp table 704; timestamp table 704 may include information describing time information pertaining to any particular search query. Timestamp table 704 may include time information such as the date, time, and/or geolocation of a user when entering or creating a search query. Timestamp table 704 may include time information such as how long a user spent creating a search query, how long a user spent reformatting a search query, and/or how long a user spent looking at search results from a search query. Timestamp table 704 may include time information such as how long a user browsed through particular items and/or products contained within system 100, as well as how long a user spent reading through a particular product and/or item detail page. One or more database tables in fingerprint database 128 may include, without limitation a browsing table 708; browsing table 708 may include information describing browsing patterns of a particular user. Browsing patterns may include what products and/or items a user may select to look at, categories of products and/or items that a user may look at, as well as products and/or items a user may select to examine from a list generated after a search query request. For example, browsing table 708 may include information such as a list of products and/or items that a user looked at during a particular search session. One or more database tables in fingerprint database 128 may include, without limitation a product detail table 712; product detail table 712 may include information describing any product and/or item details that a user may have selected to viewed. For example, product detail table 712 may include information describing a shampoo that a user selected to view more detailed information about such as ingredients or scent. In yet another non-limiting example, product detail table 712 may include information describing a towel that a user selected to view detailed information to find out if the cotton used to produce the towel was grown organically and without the use of artificial dyes. One or more database tables in fingerprint database 128 may include, without limitation a product selection table 716; product selection table 716 may include information describing one or more items and/or products that a user may select for purchase but never actually purchase. For example, product selection table 716 may include information describing one or more products and/or items that a user may place in an electronic shopping cart to purchase later. One or more database tables in fingerprint database 128 may include, without limitation a miscellaneous table 720; miscellaneous table 720 may include any other information pertaining to a previous search query, and/or user activity datum.

Figure 8:
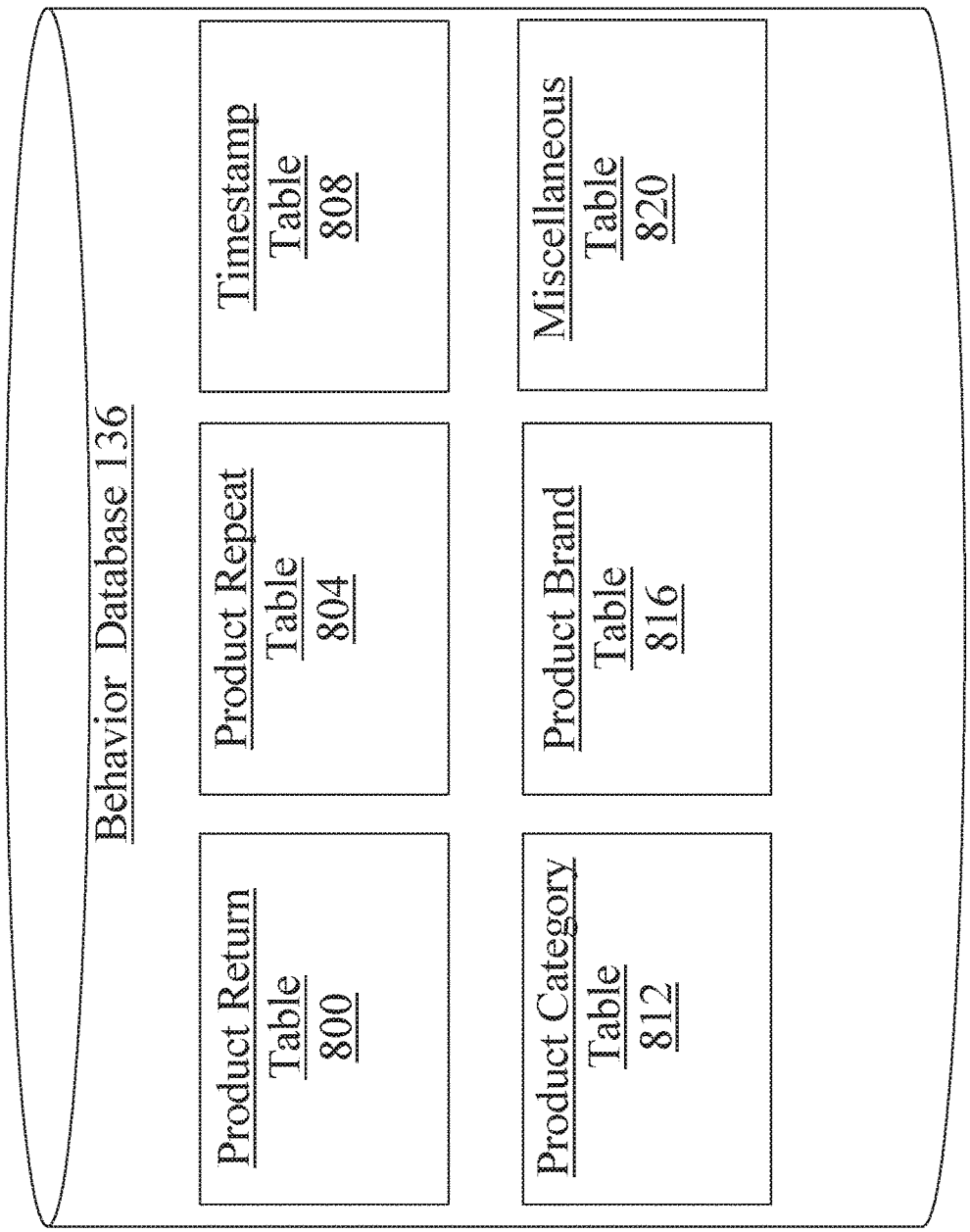
FIG. 8 is a block diagram illustrating an exemplary embodiment of a behavior database.

Referring now to FIG. 8, an exemplary embodiment of behavior database 136 is illustrated, which may be implemented in any manner suitable for implementation of biological extraction database 300. Behavior database 136 may include user behavior data, including any of the user behavior data as described above in reference to FIG. 1. One or more database tables in behavior database 136 may include product return table 800; product return table 800 may include any information describing any product and/or item that a user may have returned after purchase. For example, product return table 800 may include information describing a body lotion that a user returned after purchase and received money back or a cell phone that a user returned and received money back. Product return table 800 may include information such as an item and/or product that a user may have exchanged for a different product and/or item. For example, product return table 800 may include information such as an item and/or product that a user exchanged for credit or exchanged for a different product or item made by the same brand. One or more database tables in behavior database 136 may include product repeat table 804; product repeat table 804 may include any items and/or products that a user may have purchased on more than one occasion. For example, product repeat table 804 may include information describing a product such as a body wash that a user purchased three times or a protein bar that a user purchased seven times. One or more database tables in behavior database 136 may include timestamp table 808; timestamp table 808 may include time information such as the date, time, and/or geolocation of a product and/or item that a user purchased. For example, timestamp table 808 may include information describing the time that a user purchased a steel water container or the geo-location of a user who purchased an item such as a fragrance free bar of soap. One or more database tables in behavior database 136 may include product category table; product category table may include information describing one or more categories of products and/or items that a user previously purchased. Product categories may include any of the product categories as described herein and below in reference to FIG. 12. For example, product category table 812 may include information describing electronic purchases of a user or beauty purchases of a user. One or more database tables in behavior database 136 may include product brand table 816; product brand table 816 may include information describing particular brands of products and/or items that a user previously purchased. For example, product brand table 816 may include information describing a particular brand of toilet paper that a user purchased that was free of dyes or a particular brand of iced tea that a user purchased that was sold in a glass container. One or more database tables in behavior database 136 may include miscellaneous table 820; miscellaneous table 820 may include any other information pertaining to a user behavior data.

Figure 9:
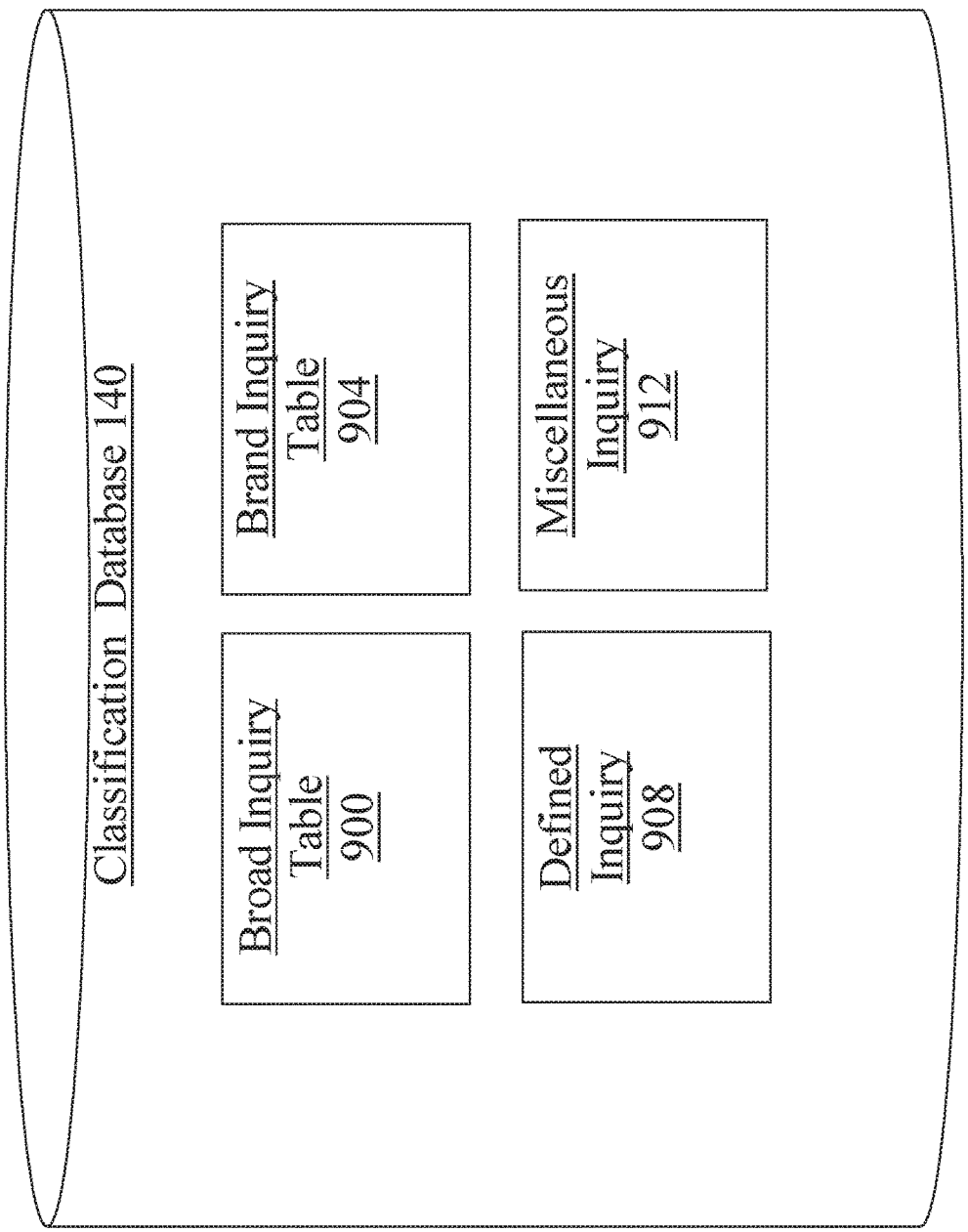
FIG. 9 is a block diagram illustrating an exemplary embodiment of a classification database.

Referring now to FIG. 9, an exemplary embodiment of classification database 140 is illustrated, which may be implemented in any manner suitable for implementation of biological extraction database 300. Classification database 140 may include any information describing classifications of search queries and/or user activity data. One or more database tables contained within classification database 140 may include broad inquiry table 900; broad inquiry table 900 may include information describing search queries and/or user activity classified as broad inquiries. Broad inquires may include any search queries and/or user activity that do not specify a particular brand or manufacturer and/or may contain a request for a category of product and/or item. For example, a search query containing "tennis racquet" may be categorized as a broad inquiry. In yet another non-limiting example, a user activity datum that includes a request for a toy may be categorized as a broad inquiry. One or more database tables contained within classification database 140 may include brand inquiry table 904; brand inquiry table 904 may include information describing search queries and/or user activity classified as brand inquiries. Brand inquiries may include any search queries and/or user activity that specify a particular brand item and/or product or a particular manufacturer of a particular item and/or product. For example, a search query containing "Dell Laptop" may be categorized as a brand inquiry. In yet another non-limiting example, a user activity datum that includes a request for "BareMinerals makeup" may be categorized as a brand inquiry. One or more database tables contained within classification database 140 may include defined inquiry table 908; defined inquiry table 908 may include information describing search queries and/or user activity classified as defined inquires. Defined inquires may include any search queries and/or user activity that specify a request for a defined item and/or product that may be contained within a category of products and/or items but may not necessarily include a request for a particular brand or manufacturer. For example, a search query containing "cast iron skillet" may be categorized as a defined inquiry. In yet another non-limiting example, a user activity datum that includes a request for "cleaning product free of phthalate" may be categorized as a defined inquiry. One or more database tables contained within classification database 140 may include miscellaneous inquiry table 912; miscellaneous inquiry table 912 may include any inquiry that may not be categorized according to one of the categories as described herein.

Figure 10:
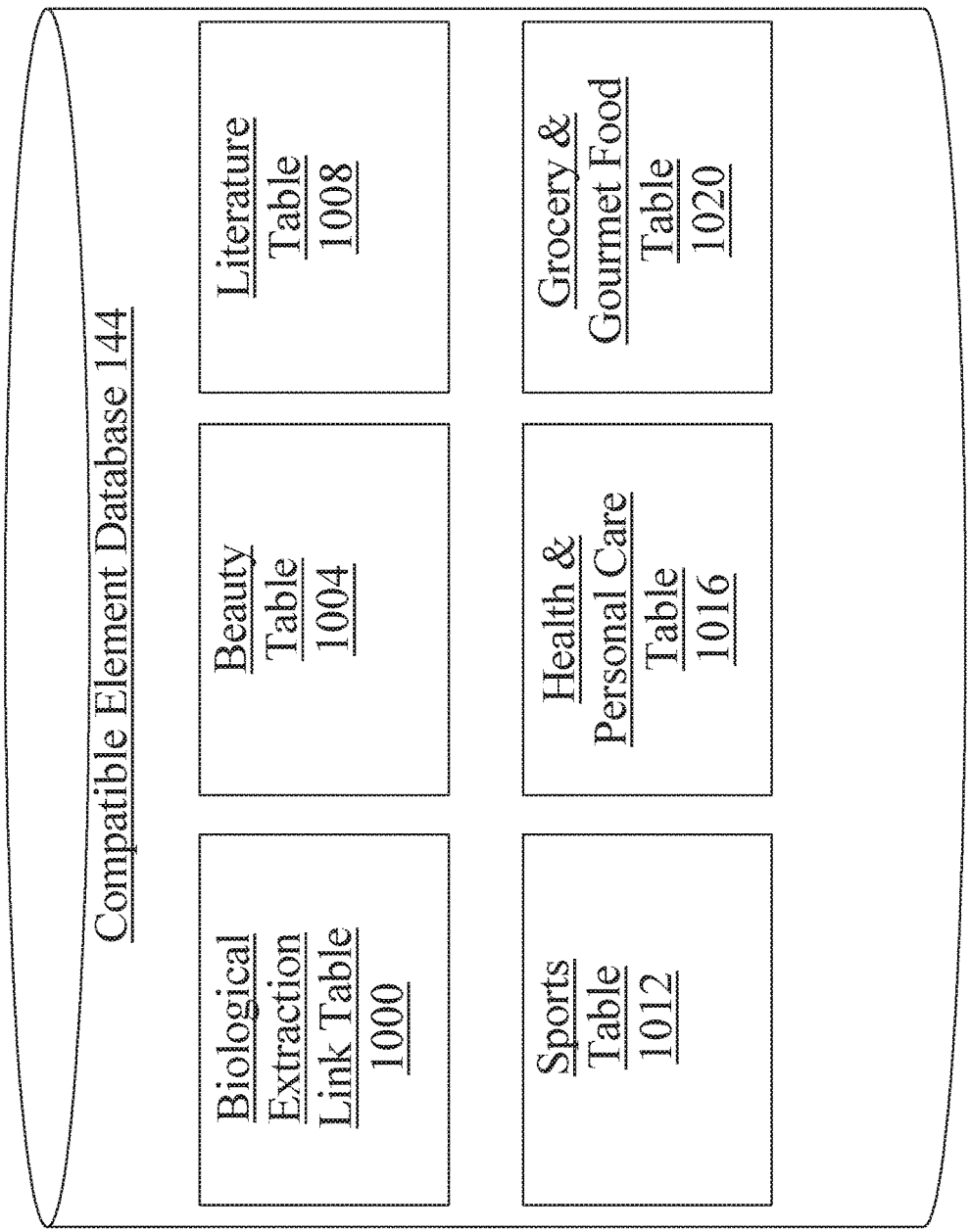
FIG. 10 is a block diagram illustrating an exemplary embodiment of a compatible element database.

Referring now to FIG. 10, an exemplary embodiment of compatible element database 144 is illustrated, which may be implemented in any manner suitable for implementation of biological extraction database 300. Compatible element database 144 may, as a non-limiting example, organize data stored in compatible element database 144 according to one or more database tables. For instance, a common column between two tables of compatible element database 144 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

With continued reference to FIG. 10, compatible element database 144 may include a biological extraction link table 1000; biological extraction link table 1000 may link biological extraction data to compatible element data, using any suitable method for linking data in two or more tables as described above. Compatible element database 144 may include beauty table 1004; beauty table 1004 may include beauty products compatible with a given biological extraction. For example, beauty table 1004 may include information describing brands of makeup that may be free of parabens and heavy metals for a user with heavy metal toxicity. Compatible element database 144 may include literature table 1008; literature table 1008 may include information describing literature compatible with a given biological extraction. For example, literature table 1008 may include a list of books, magazines, brochures, articles, pamphlets, and/or other reading materials that may be suitable for a user with a given biological extraction. For example, literature table 1008 may include a motivational book for a user with depression or an article describing different spiritual practices for a user with cancer. Compatible element database 144 may include sports table 1012; sports table 1012 may include information describing sporting equipment that may be compatible for a user with a given biological extraction. For example, sports table 1012 may include information such as golf clubs, golf balls, and croquet rackets for a user with kidney disease or a user who has only one kidney and has prohibitions on playing contact sports. In yet another non-limiting example, sports table 1012 may include information such as tennis rackets, tennis balls, and jogging sneakers for a user with cardiovascular disease. Compatible element database 144 may include health and personal care table 1016; health and personal care table 1016 may include information describing health and personal care products that may be compatible for a user with a given biological extraction. For example, health and personal care table 1016 may include information such as possible shampoos, conditioners, body wash, tooth paste and the like that do not contain synthetic estrogens or estrogen mimicking compounds for a user with CYP19A1 gene mutation. Compatible element database 144 may include grocery and gourmet food table 1020; grocery and gourmet food table 1020 may include information describing grocery items and foods that may be compatible for a user with a given biological extraction. For example, grocery and gourmet food table 1020 may include information such as food products such as crackers, cookies, and snacks that do not contain dairy for a user with a mutation in MCM6 gene responsible for lactase enzyme production. Compatible element database 144 may include a single table and/or a plurality of tables; plurality of tables may include tables for particular categories of compatible elements such as but not limited to books, beauty, electronics, health, musical instruments, toys and games, jewelry, home and garden, outdoors, (not shown), to name a few non-limiting examples presented for illustrative purposes only.

Figure 11:
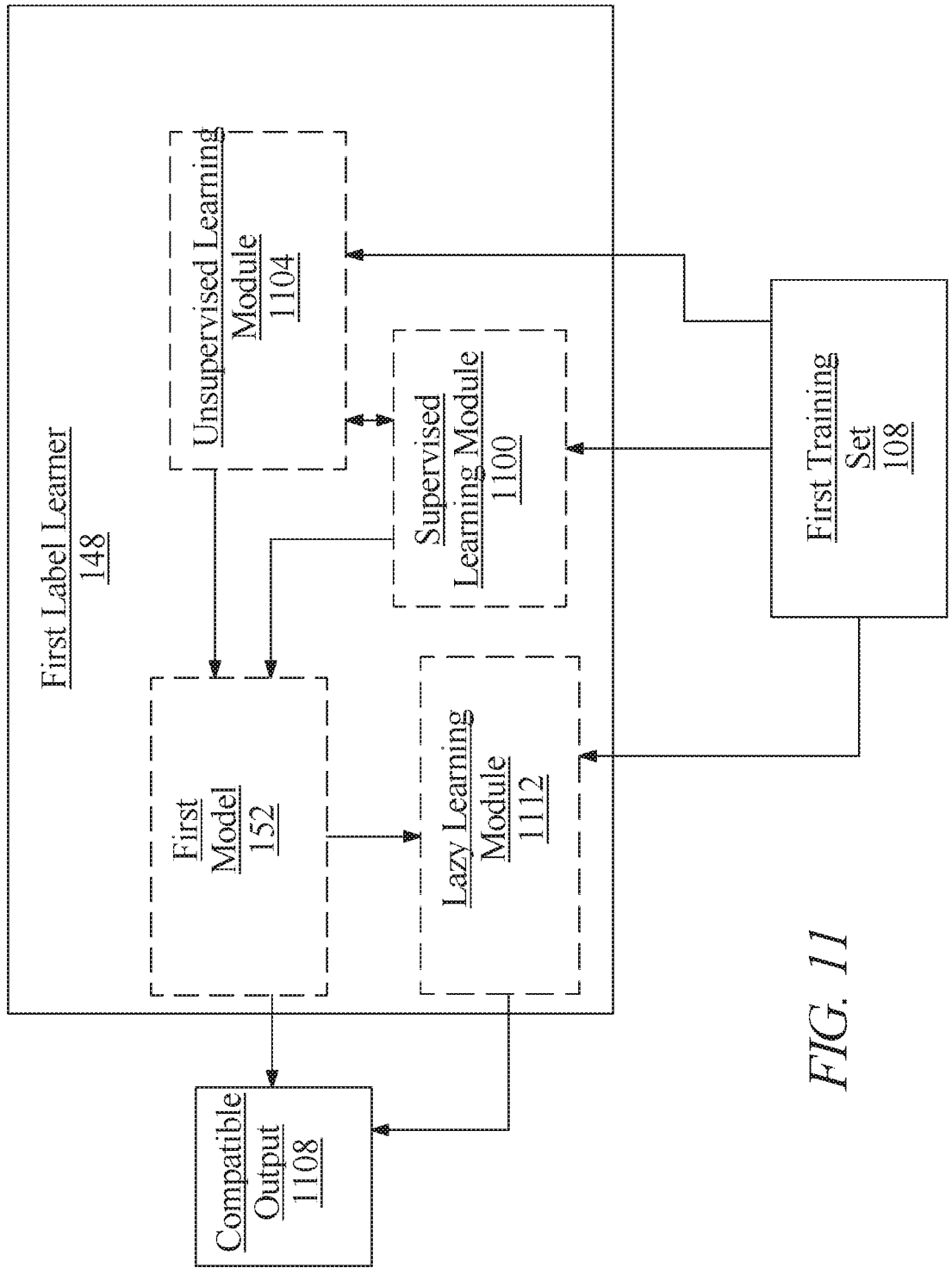
FIG. 11 is a block diagram illustrating an exemplary embodiment of a first label learner.

Referring now to FIG. 11, an exemplary embodiment of first label learner 148 is illustrated. Machine-learning algorithms used by first label learner 148 may include supervised machine-learning algorithms, which may, as a non-limiting example be executed using a supervised learning module 1100 executing on at least a server 104 and/or on another computing device in communication with at least a server 104, which may include any hardware or software module. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may use elements of physiological data 112 as inputs, compatible labels 116 as outputs, and a scoring function representing a desired form of relationship to be detected between elements of physiological data 112 and compatible labels 116; scoring function may, for instance, seek to maximize the probability that a given element of physiological data 112 and/or combination of elements of physiological data is associated with a given compatible label 116 and/or combination of compatible labels 116 to minimize the probability that a given element of physiological data 112 and/or combination of elements of physiological data is not associated with a given compatible label 116 and/or combination of compatible labels 116. Scoring function may be expressed as a risk function representing an "expected loss" of an algorithm relating inputs to outputs, where loss is computed as an error function representing a degree to which a prediction generated by the relation is incorrect when compared to a given input-output pair provided in first training set. Persons skilled in the art, upon reviewing the entirety of this disclosure, will be aware of various possible variations of supervised machine learning algorithms that may be used to determine relations between elements of physiological data 112 and compatible labels 116. In an embodiment, one or more supervised machine-learning algorithms may be restricted to a particular domain for instance, a supervised machine-learning process may be performed with respect to a given set of parameters and/or categories of parameters that have been suspected to be related to a given set of compatible labels 116, and/or are specified as linked to a medical specialty and/or field of medicine covering a particular set of compatible label 116. As a non-limiting example, a particular set of blood test biomarkers may be typically used to eliminate certain compatible elements such as for example positive BRACA 1 or BRACA 2 gene mutations and a need to eliminate certain known breast cancer causing chemicals such as bisphenol A and phthalates, and a supervised machine-learning process may be performed to relate those blood test biomarkers to the correlated compatible products; in an embodiment, domain restrictions of supervised machine-learning procedures may improve accuracy of resulting models by ignoring artifacts in training data. Domain restrictions may be suggested by experts and/or deduced from known purposes for particular evaluations and/or known tests used to evaluate compatible label 116. Additional supervised learning processes may be performed without domain restrictions to detect, for instance, previously unknown and/or unsuspected relationships between physiological data 112 and compatible label 116.

With continued reference to FIG. 11, machine-learning algorithms may include unsupervised processes; unsupervised processes may, as a non-limiting example, be executed by an unsupervised learning module 1104 executing on at least a server 104 and/or on another computing device in communication with at least a server 104, which may include any hardware or software module. An unsupervised machine-learning process, as used herein, is a process that derives inferences in datasets without regard to labels; as a result, an unsupervised machine-learning process may be free to discover any structure, relationship, and/or correlation provided in the data. For instance, and without limitation, first label learner 148 and/or at least a server 104 may perform an unsupervised machine learning process on first training set, which may cluster data of first training set 108 according to detected relationships between elements of the first training set, including without limitation correlations of elements of physiological data 112 to each other and correlations of compatible label 116 to each other; such relations may then be combined with supervised machine learning results to add new criteria for first label learner 148 to apply in relating diagnostic output to compatible label 116. As a non-limiting, illustrative example, an unsupervised process may determine that a first element of user physiological data acquired in a blood test correlates closely with a second element of user physiological data, where the first element has been linked via supervised learning processes to a given compatible label 116, but the second has not; for instance, the second element may not have been defined as an input for the supervised learning process, or may pertain to a domain outside of a domain limitation for the supervised learning process. Continuing the example a close correlation between first element of user physiological data and second element of user physiological data may indicate that the second element is also a good predictor for the compatible label 116; second element may be included in a new supervised process to derive a relationship or may be used as a synonym or proxy for the first physiological data element by first label learner 148.

Still referring to FIG. 11, at least a server 104 and/or first label learner 148 may detect further significant categories of user physiological data, relationships of such categories to compatible labels 116, and/or categories of compatible labels 116 using machine-learning processes, including without limitation unsupervised machine-learning processes as described above; such newly identified categories, as well as categories entered by experts in free-form fields as described above, may be added to pre-populated lists of categories, lists used to identify language elements for language processing module 124, and/or lists used to identify and/or score categories detected in documents, as described above. In an embodiment, as additional data is added to system 100, first label learner 148 and/or at least a server 104 may continuously or iteratively perform unsupervised machine-learning processes to detect relationships between different elements of the added and/or overall data; in an embodiment, this may enable system 100 to use detected relationships to discover new correlations between known biomarkers, and/or compatible labels 116 and one or more elements of data in large bodies of data, such as genomic, proteomic, and/or microbiome-related data, enabling future supervised learning and/or lazy learning processes as described in further detail below to identify relationships between, e.g., particular clusters of genetic alleles and particular compatible labels 116 and/or suitable compatible labels 116. Use of unsupervised learning may greatly enhance the accuracy and detail with which system may detect compatible label 116.

With continued reference to FIG. 11, unsupervised processes may be subjected to domain limitations. For instance, and without limitation, an unsupervised process may be performed regarding a comprehensive set of data regarding one person, such as a comprehensive medical history, set of test results, and/or physiological data such as genomic, proteomic, and/or other data concerning that persons. As another non-limiting example, an unsupervised process may be performed on data concerning a particular cohort of persons; cohort may include, without limitation, a demographic group such as a group of people having a shared age range, ethnic background, nationality, sex, and/or gender. Cohort may include, without limitation, a group of people having a shared value for an element and/or category of physiological data, a group of people having a shared value for an element and/or category of compatible label 116; as illustrative examples, cohort could include all people having a certain level or range of levels of blood triglycerides, all people diagnosed with anxiety, all people with a SRD5A2 gene mutation, or the like. Persons skilled in the art, upon reviewing the entirety of this disclosure, will be aware of a multiplicity of ways in which cohorts and/or other sets of data may be defined and/or limited for a particular unsupervised learning process.

Still referring to FIG. 11, first label learner 148 may alternatively or additionally be designed and configured to generate at least a compatible output 1108 by executing a lazy learning process as a function of the first training set 108 and/or at least a biological extraction; lazy learning processes may be performed by a lazy learning module 1112 executing on at least a server 104 and/or on another computing device in communication with at least a server 104, which may include any hardware or software module. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover a "first guess" at a compatible label 116 associated with a user physiological test sample, using first training set. As a non-limiting example, an initial heuristic may include a ranking of compatible label 116 according to relation to a test type of at least a physiological test sample, one or more categories of physiological data identified in test type of at least a physiological test sample, and/or one or more values detected in at least a physiological test sample; ranking may include, without limitation, ranking according to significance scores of associations between elements of physiological data 112 and compatible label 116, for instance as calculated as described above. Heuristic may include selecting some number of highest-ranking associations and/or compatible label 116. First label learner 148 may alternatively or additionally implement any suitable "lazy learning" algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate compatible outputs 1108 as described in this disclosure, including without limitation lazy learning applications of machine-learning algorithms as described in further detail below.

Figure 12:
FIG. 12 is a block diagram illustrating an exemplary embodiment of a product category list.

Referring now to FIG. 12, an exemplary embodiment of product categories 1200 is illustrated. Product categories may include products and/or items having shared characteristics. In an embodiment, product categories may be displayed to a user such as through graphical user interface 120. In an embodiment, a user may select a product category such as through graphical user interface 120 from a drop-down menu and submit a search query directed towards a particular product category. Product categories may include but are not limited to automotive, baby products, beauty, books, business products, camera and photo, cell phones, clothing, collectible coins, electronics, jewelry, fine art, grocery and gourmet food, handmade products, historical collectibles, home and garden, health and personal care, luggage and travel accessories, music, office products, outdoors, shoes, handbags, sports, toys, and watches. In an embodiment, product categories may be organized into sub-categories. For example and without limitation, beauty products may be separated into further sub-categories to include makeup, skin care, hair care, fragrance, foot hand and nail care, tools and accessories, shave and hair removal, personal care, and oral care. In an embodiment, sub-categories may be further broken down into further sub-categories that share certain attributes including but not limited to natural, organic, cruelty free, paraben free, hypoallergenic, unscented, alcohol free and the like. In yet another non-limiting example, a product category such as electronics may be further organized into sub-categories that include computers and accessories, tv and video, cell phones and accessories, home audio, headphones, office electronics, office supplies, smart home, musical instruments, and video games. In such an instance, a sub-category such as computers and accessories may be further broken down into further sub-categories including desktops, laptops, tablets, monitors, computer accessories, computer components, drives and storage, networking, office supplies, printers, and gaming.

Figure 13:
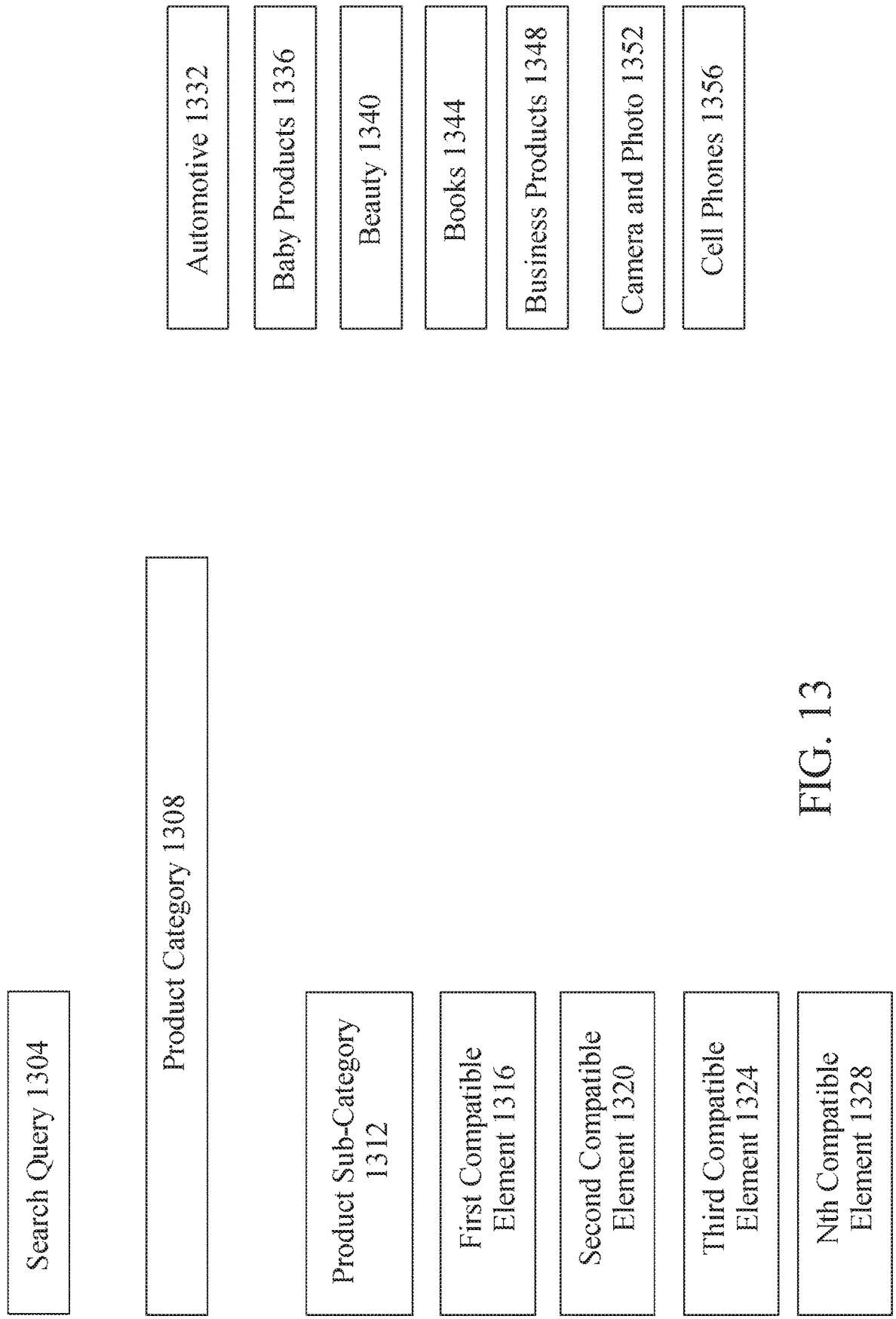
FIG. 13 is a block diagram illustrating an exemplary embodiment of a graphical user interface.

Referring now to FIG. 13, an exemplary embodiment of a graphical user interface 1300 is illustrated. For example and illustrative purposes only, graphical user interface 120 may include a screen whereby a user may enter a search query to search for products and/or items contained within system 100. In an embodiment, and for illustrative purposes only GUI 120 may include a search query field 1304 whereby a user can enter a search query. In an embodiment, search query field 1304 may include a drop-down menu of choices based on previous user entries. Textual inputs entered into search query field 1304 may be utilized to create user activity datums. Previous search queries including previous entries into search query field 1304 may be stored in fingerprint database 128. GUI 120 may include product category field 1308 whereby a user may enter and/or select a product category. Product category may include any of the product categories as described herein, including any of the product categories described above in reference to FIG. 12. GUI 120 may include product sub-category field 1312, which a user may enter and/or select a sub-category related to product category field 1308. In an embodiment, product sub-category may be auto-generated into a list based on entered and/or selected product category field 1308. GUI 120 may display first compatible element 1316. GUI 120 may display second compatible element 1320, and third compatible element 1324. GUI 120 may display nth compatible element 1328 such as for example when there are multiple compatible elements. In an embodiment, compatible elements may be ranked according to a particular ranking scheme such as by percentage of compatibly, with highest percentage compatible elements ranked at the top and descending compatible elements listed in descending order. GUI 120 may include product categories that a user may click on to find compatible elements contained within categories. Categories may include for illustrative purposes only automotive 1332, baby products 1336, beauty 1340, books 1344, business products 1348, camera and photo 1352, and cell phones 1356. Categories that a user may click upon may include any of the categories described herein, including any of the categories as listed above in reference to FIG. 12.

Figure 14:
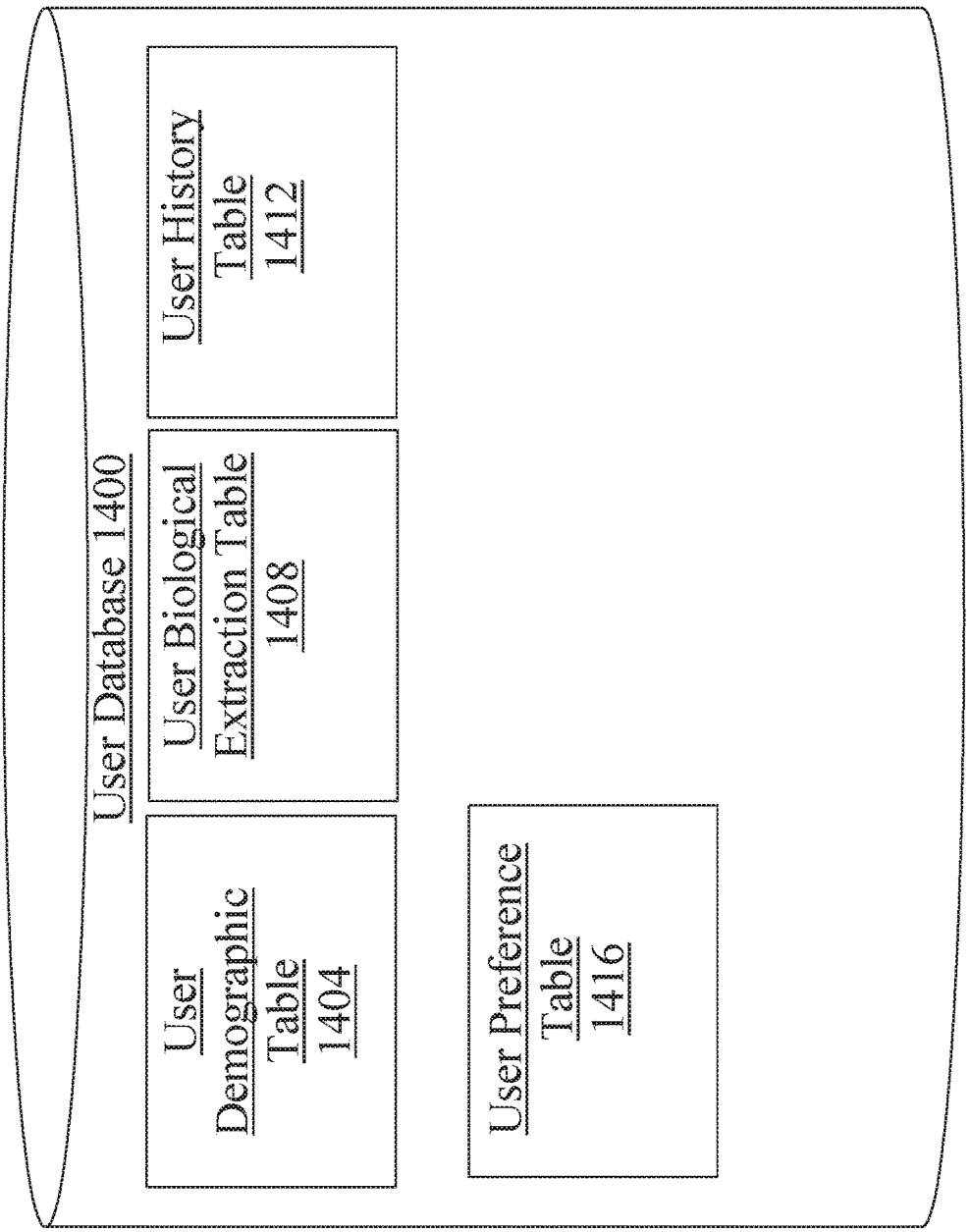
FIG. 14 is a block diagram illustrating an exemplary embodiment of a user database.

Referring now to FIG. 14, an exemplary embodiment of user database 1400 is illustrated, which may be implemented in any manner suitable for implementation of biological extraction database 300. User database 1400 may include user information and/or user preferences that may be utilized by at least a server 104 when selecting at least a first compatible element. In an embodiment, first learner 148 148 may utilize data stored within user database 1400 to generate user specific training sets. One or more database tables in user database 1400 may include, without limitation, a user demographic table 1404; user demographic table 1404 may include information describing demographic information pertaining to user. For example, demographic table 1404 may include information describing user's name, address, phone number, race, gender, marital status, education level, employment information, total income, and the like. One or more database tables in user database 1400 may include, without limitation, a user biological extraction table 1408; user biological extraction table 1408 may include information and/or data stored about one or more biological extractions from a user. For example, user biological extraction table 1408 may include information describing results from a user's blood test or results from a saliva test. In an embodiment, user biological extraction table 1408 may be organized and/or categorized such as in chronological order, and/or by extraction type. One or more database tables in user database 1400 may include, without limitation, a user history table 1412; user history table 1412 may include information regarding history of user's interactions with system 100. For example, user history table 1412 may include data describing previous purchases a user made or previous products and/or items user browsed. In an embodiment, user history table 1412 may include any of the user history information contained within fingerprint database 128. In yet another non-limiting example, user history table 1412 may include information such as products and/or ingredients that a user placed into an electronic shopping cart or electronic shopping basket and possibly saved for later or later came back and purchased. One or more database tables in user database 1400 may include, without limitation, user preference table 1416; user preference table 1416 may include information describing a user's preference for particular products, ingredients, and/or brands of products or ingredients. For example, user preference table 1416 may include information describing user's preference for a particular brand of shampoo user routinely purchases or user's preference for a particular company's line of cleaning products. In an embodiment, user preference table 1416 may include information regarding a user's preference for a particular product or ingredient based on a ranking or review that user may have attributed to a particular product or ingredient. Information contained within user database 1400 may be obtained from user client device 156 156 and/or through information provided through graphical user interface 120.

Referring now to FIG. 15, an exemplary embodiment of compatible element similarity index value database 1500 is illustrated, which may be implemented in any manner suitable for implementation of biological extraction database 300. Similarity index value database 1500 may include information describing similarity index values for different products and/or items. Similarity index value database 1500 may be consulted by at least a server 104 when selecting at least a compatible element. Similarity index is a value assigned to a compatible element indicating a degree of similarity between a first compatible element and a second compatible element. Similarity may include a degree of likeness between a first compatible element and a second compatible element. Similarity index value may contain information allowing for at least a server 104 to select one or more compatible elements that are similar in response to a particular search query. For example, similarity index value may be utilized by at least a server 104 to select multiple products that may be suggested to a user with a search query such as "wagon for young children" or a search query such as "hair conditioner free of ammonia." Similarity index value may also be utilized to suggest other products and/or items such as when a product and/or item may not be in stock, may be on backorder, may be too expensive for a user and the like. Similarity index value database 1500 may be organized into categories of compatible elements. Categories may include categories of products and/or items. In an embodiment, categories may include categories describing functionality and/or utility of different compatible elements.

With continued reference to FIG. 15, one or more database tables in compatible element similarity index value database 1500 may include, without limitation beauty table 1504; beauty table 1504 may include similarity index values for all compatible elements categorized as beauty. For example, beauty table 1104 may include similarity index values for compatible elements such as for example, skin serum, retinol cream, face wash, makeup brushes, shaving cream, face masks, face spray, eye cream, and the like. In an embodiment, compatible elements contained within beauty table 1504 may be further categorized into sub-categories such as tools, eye products, face products, body products, hair products, female beauty products, male beauty products, and the like. One or more database tables in compatible element similarity index value database 1500 may include, without limitation books table 1508; books table 1508 may include similarity index values for all compatible elements categorized as books. For example, books table 1508 may include similarity index values for compatible elements such as biographies & memoirs, children's books, history books, law books, medical books, mystery books, romance books, religious books, science fiction books, self-help books, sports & outdoor books, teen & young adult books, travel books and the like. In an embodiment, books table 1508 may be further categorized into sub-categories such as award winners, top sellers, new releases, bargain books, top twenty lists, celebrity picks, local authors, and the like. One or more database tables in compatible element similarity index value database 1500 may include, without limitation electronics table 1512; electronics table 1512 may include similarity index values for all compatible elements categorized as electronics. For example, electronics table 1512 may include similarity index values for compatible elements such as computers, printers, headphones, televisions, projectors, cell phones, tablets, video games, and the like. In an embodiment, electronics table 1512 may be further categorized into sub-categories such as devices, smart home devices, television, camera, computers, accessories, car electronics, portable electronics, software, video games, and the like. One or more database tables in compatible element similarity index value database 1500 may include, without limitation grocery and gourmet foods table 1516; grocery and gourmet foods table 1516 may include similarity index values for all compatible elements categorized as grocery and gourmet foods. For example, grocery and gourmet foods table 1516 may include similarity index values for compatible elements such as foods, beverages, food storage products, food replacements and the like. In an embodiment, groceries and gourmet foods table 1516 may be further categorized into sub-categories such as baby food, alcoholic beverages, beverages, breads and bakery, breakfast foods, candy, chocolate, dairy, cheese, plants, meal kits, frozen, meat, seafood, meat substitutes, pantries staples, and the like. One or more database tables in compatible element similarity index value database 1500 may include, without limitation home and garden table 1520; home and garden table 1520 may include similarity index value for compatible elements such as plants, seeds, garden equipment, outdoor equipment, and the like. In an embodiment, home and garden table 1520 may be further categorized into sub-categories such as plants, seeds, bulbs, patio furniture, patio seating, canopies, gazebos, planters, outdoor lighting, lawn mowers, outdoor power tools, garden sculptures, grills, and gardening tools. One or more database tables in compatible element similarity index value database 1500 may include, without limitation music table 1524; music table 1524 may include similarity index values for compatible elements such as specific songs, artists, albums, and the like. In an embodiment, music table 1524 may be further categorized into sub-categories such as Christian contemporary music, country, rap, jazz, rock, pop, classical, Broadway vocalists, R & B, vocal pop, and the like. Information contained within compatible element similarity index value database 1500 may be obtained from user client device 156 156 and/or through information provided through graphical user interface 120. Compatible element similarity index value database 1500 may include a single table and/or a plurality of tables; plurality of tables may include tables for particular categories of compatible elements such as health and personal care, outdoors, automotive, baby products, camera and photo, cell phone and accessories, entertainment, art, design, appliances, musical instruments, office products, personal computers, sports, sport collectibles, tools and home (not shown), to name a few non-limiting examples presented for illustrative purposes only.

Figure 16:
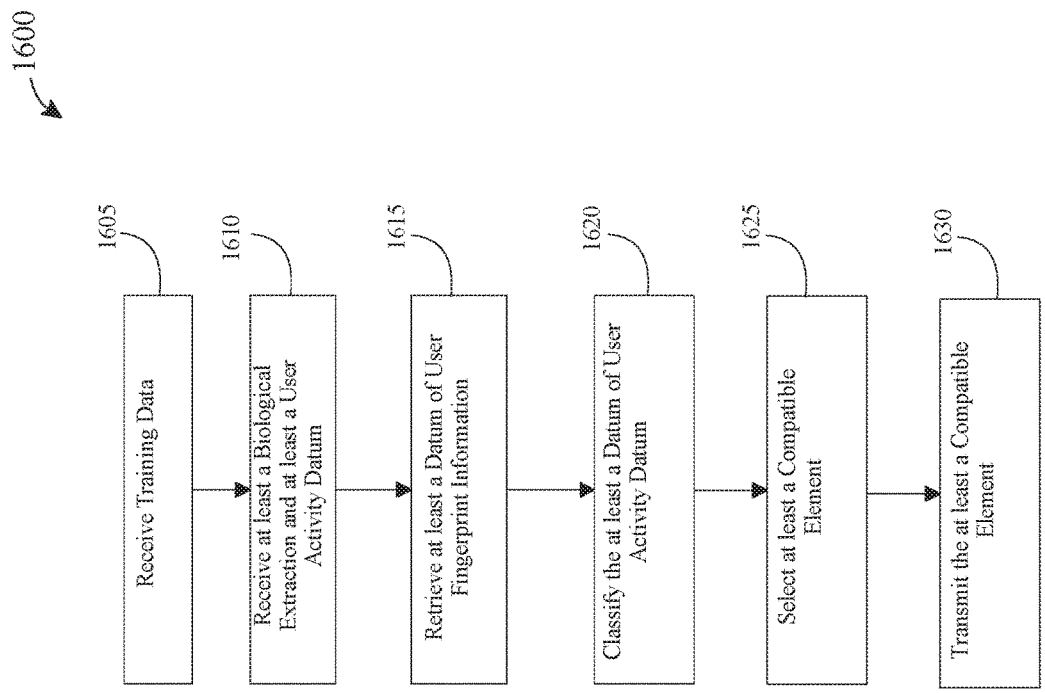
FIG. 16 is a process flow diagram illustrating an exemplary embodiment of a method of using artificial intelligence to analyze user activity data.

Referring now to FIG. 16, an exemplary embodiment of a method 1600 of using artificial intelligence to analyze user activity data is illustrated. At step 1605 at least a server receives training data. Receiving training data may include receiving a first training set 108 including a plurality of first data entries, each first data entry of the plurality of first data entries including at least an element of physiological state data 112 and at least a correlated compatible label 116. Element of physiological state data 112 may include any of the physiological state data 112 as described above in reference to FIGS. 1-16. Correlated compatible label 116 may include any of the correlated compatible label 116 as described above in reference to FIGS. 1-16. In an embodiment, receiving first training set 108 may include associating the at least an element of physiological state data 112 with at least a category from a list of significant categories of physiological state data 112. In an embodiment, significant categories may be received from an expert as described above in reference to FIG. 1. Receiving training data may be performed utilizing any of the methodologies as described above in reference to FIGS. 1-16.

With continued reference to FIG. 16, at step 1610 at least a server receives from a user at least a biological extraction and at least a user activity datum. Biological extraction may include any of the biological extractions as described above in reference to FIG. 1013. For instance and without limitation, receiving at least a biological extraction may including receiving a datum of information describing a particular genetic mutation or a particular diagnosed condition of a user. For example, at least a server 104 may receive at least a biological extraction describing a user's MCM6 mutation impairing a user's ability to produce the lactase enzyme. In an embodiment, at least a biological extraction may be stored by at least a server 104 such as in a memory component. In an embodiment, at least a server 104 may record at least a biological extraction from a user. Recording at least a biological extraction may be performed utilizing any of the methodologies as described above in reference to FIGS. 1-16. In an embodiment, at least a biological extraction received from a user may be utilized by at least a server to generate diagnostic output as a function of the training data and the at least a biological extraction. In an embodiment, diagnostic output may be generated by a diagnostic engine 160 operating on at least a server. In such an instance, at least a compatible element may be selected as a function of the at least a diagnostic output.

With continued reference to FIG. 16, at least a server receives at least a user activity datum. User activity datum may include any of the user activity datums as described above in reference to FIGS. 1-16. In an embodiment, at least a user activity datum may include receiving a user search query such as text that a user searched for. For example, at least a user activity datum may include a user search query such as "wide brimmed hat" or "fragrance free body lotion." In an embodiment, at least a user activity datum may include timestamp information such as how long a user searched for a particular product and/or item. In an embodiment, at least a user activity datum may include any actions performed by a user in relation to a query such as for example, a reformulation of a query, a term swap, a term addition, a term deletion, an abandonment of a query, a scope change, and the like. At least a user activity datum may be received using any methodologies described herein, including any network methodologies as described below in reference to FIG. 17.

With continued reference to FIG. 16, at step 1615 at least a server retrieves from a fingerprint database 128 at least a datum of user fingerprint information. Fingerprint database 128 may include any of the fingerprint databases 128 as described above in reference to FIG. 1 and FIG. 7. Fingerprint database 128 may include stored fingerprint data 132. Stored fingerprint data 132 may include any of the fingerprint data 132 as described above in reference to FIG. 1 and FIG. 7. Fingerprint data 132 may include for example, data identifying one or more actions performed by a user in relation to a search query during a search session. Fingerprint data 132 may include timestamps including any of the timestamps as described above in reference to FIGS. 1-16. For example, fingerprint data 132 may include information describing how long a user examined a particular product information page or how long a user spent reformatting a search query. In an embodiment, at least a server may include a parsing module that may extract at least an element from the at least a user activity datum wherein the at least an element further comprises at least a compatible element neutralizer and retrieve at least a datum of user fingerprint data 132 as a function of the at least an element. Compatible element neutralizer may include any of the compatible element neutralizers as described above in reference to FIG. 1. In an embodiment, compatible element neutralizer may be utilized to select and/or not select at least a compatible element. For example, a compatible element neutralizer such as a treatment with a blood thinning medication such as warfarin may be utilized to not select at least a compatible element such as a multi-vitamin that contains Vitamin K. In yet another non-limiting example, a compatible element neutralizer such as treatment with warfarin may be utilized to select at least a compatible element such as a multi-vitamin that does not contain Vitamin K. Parsing module is configured to extract at least an element where the element further comprises at least a compatible element neutralizer from at least a user activity datum and retrieve at least a datum of user fingerprint data as a function of the at least an element. For example, compatible element neutralizer containing a course of treatment of a specific length in duration may be utilized to retrieve at least a user fingerprint datum pertinent to the duration of treatment with the compatible element neutralizer. Such information may be utilized to select and/or recommend compatible elements that a user may utilize, and which may be pertinent to a user's browsing history and selection during which time a compatible element neutralizer is imposed on a user. In an embodiment, element may include certain textual inputs, words, string of words, characters, and/or numerical values that may be utilized to retrieve at least a datum of user fingerprint data 132. For example, element may include a certain time period to retrieve, or a particular product or product category to retrieve. In an embodiment, at least an element may include certain information identifying a user that may be utilized by at least a server to retrieve at least a datum of user fingerprint data 132. For instance and without limitation, user may be identified by a cryptographically secure numerical code that may be contained within at least an element and matched to at least a datum of user fingerprint data 132 to confirm user identity.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

With continued reference to FIG. 16, at least a server may receive at least a user activity datum and retrieve from a behavior database 136 at least a datum of user behavior data. At least a user activity datum may include any of the datums of user activity as described above in reference to FIGS. 1-16. Behavior database 136 may include any of the behavior databases 136 as described above in reference to FIG. 1 and FIG. 8. In an embodiment, behavior database 136 may include behavior data describing purchasing history and trends of a user. For example, behavior database 136 may include data describing products and/or items that a user may have returned. In yet another non-limiting example, behavior database 136 may include data describing repeated purchases of products and/or items of a user. For example, data describing a user's purchase of the same hand soap three times in the past six weeks may be stored within behavior database 136. Behavior database 136 may include data describing particular brands that a user may have purchased in the past. User behavior data including timestamp data may also be retrieved from behavior database 136.

With continued reference to FIG. 16, at step 1620 at least a server classifies at least a user activity datum as a function of the at least a datum of user fingerprint information. Classification of at least a datum user activity may include any of the classification methodologies as described above in reference to FIG. 1 and FIG. 9. In an embodiment, classification categories may be stored in classification database 140 as described above in more detail in reference to FIG. 9. In an embodiment, at least a user activity datum may be classified as a "broad inquiry" such as when at least a user activity datum includes a nonspecific request for a product and/or item such as a product category. For example, at least a user activity datum that includes a search query for "electronics" may be classified as broad. In an embodiment, at least a user activity datum may be classified as "brand inquiry" such as when at least a user activity datum contains a request for a particular brand product and/or item such as "Louis Vuitton wallet" or "Apple TV." In an embodiment, at least a user activity datum may be classified by matching at least a datum of user fingerprint information to at least a datum of previous user activity. In such an instance, classifications may be customized to any particular user and user's search query histories. For example, at least a user activity datum that is categorized as "broad" for one user may be categorized as a defined inquiry for another user based on previous user fingerprint information and previous categorization of user activity datums. In an embodiment, at least a user activity datum may be classified as a function of receiving at least a datum of modified user activity. Modified user activity may include any of the modified user activity as described above in reference to FIGS. 1-16. For example, at least a user activity datum that is subsequently modified such as reformulating a search query or swapping a term may be reclassified as a function of a modified user activity. For example, at least a user activity datum may initially be classified as "broad" and may subsequently be modified to include a brand name product leading to the modified user activity datum to be subsequently classified as "brand."

With continued reference to FIG. 16, at step 1625 at least a server selects at least a compatible element as a function of the at least a user activity datum and the training data. Selecting at least a compatible element may include using a machine-learning algorithm and the training set. Machine-learning algorithm may include any of the machine-learning algorithms as described above in reference to FIGS. 1-16. Training data may include any of the training data as described above in reference to FIGS. 1-16. Selecting at least a compatible element may include selecting at least a compatible element as a function of a compatible element category. Compatible element category may include any of the compatible element categories as described above in reference to FIGS. 1-16. In an embodiment, compatible element category may include any of the compatible element categories as described above in reference to FIG. 12. Selecting at least a compatible element may include retrieving at least a compatible element similarity index value from a database and selecting at least a compatible element as a function of the compatible element similarity index value. Compatible element similarity index value may include any of the compatible element similarity index values as described above in reference to FIG. 1. In an embodiment, compatible element similarity index value may be stored in compatible element similarity index value database as described above in more detail in reference to FIG. 10.

With continued reference to FIG. 16, at least a server is further configured to store at least a user activity datum in fingerprint database 128. Storing at least a user activity datum in fingerprint database 128 may provide a feedback mechanism whereby subsequent user activity datums are subsequently stored after at least a server receives at least a user activity datum. In an embodiment, training data that is specific to a particular user may be stored in fingerprint database 128. In an embodiment, information that has been updated within fingerprint database 128 may be utilized to update training sets. In an embodiment, training data may be continuously updated with subsequently received biological extractions and compatibility labels.

With continued reference to FIG. 16, at step 1630 at least a server transmits the at least a compatible element to a user client device 156. User client device 156 may include any of the user client devices 156 as described herein. Transmission may occur using any of the transmission methodologies as described herein, including transmission methodologies as described below in reference to FIG. 17.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 17:
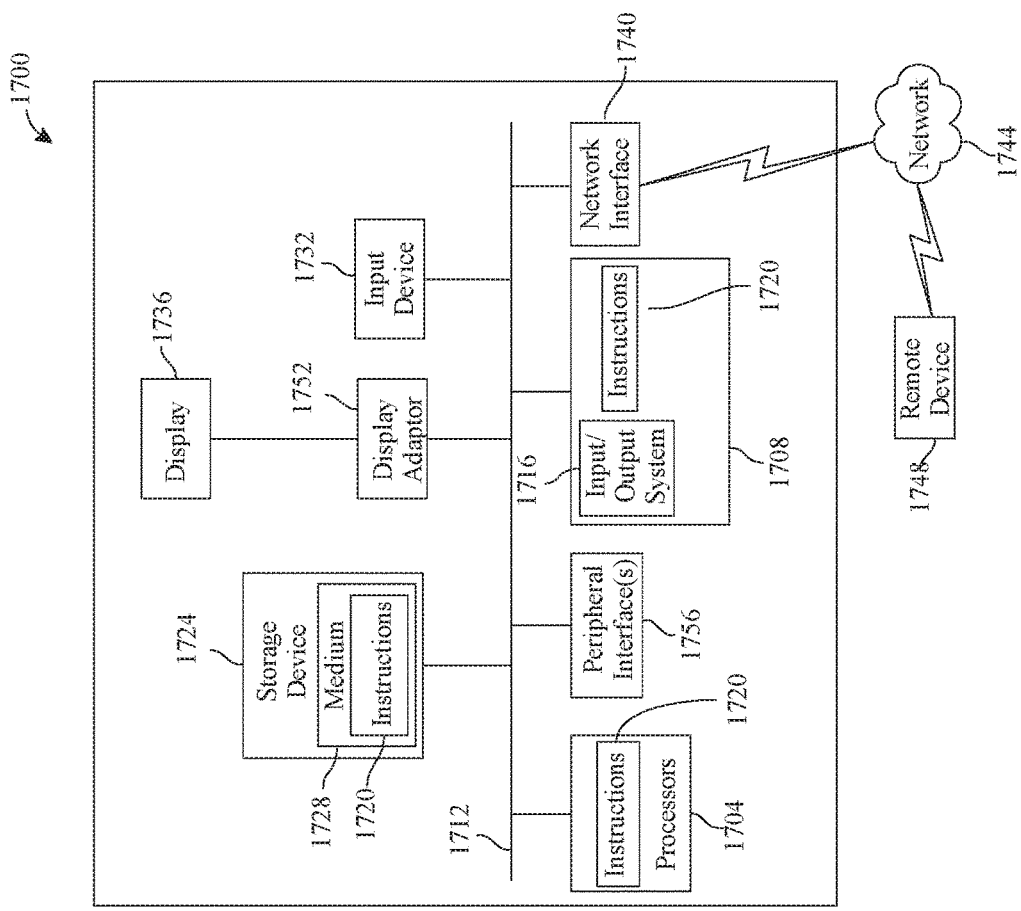
FIG. 17 is a block diagram of a computing system that can be used to implement any one or more of the methodologies disclosed herein and any one or more portions thereof.

FIG. 17 shows a diagrammatic representation of one embodiment of a computing device in the exemplary form of a computer system 1700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1700 includes a processor 1704 and a memory 1708 that communicate with each other, and with other components, via a bus 1712. Bus 1712 may include any of several types of bus structures including, but not limited to, a memory bus, a memory controller, a peripheral bus, a local bus, and any combinations thereof, using any of a variety of bus architectures.

Memory 1708 may include various components (e.g., machine-readable media) including, but not limited to, a random access memory component, a read only component, and any combinations thereof. In one example, a basic input/output system 1716 (BIOS), including basic routines that help to transfer information between elements within computer system 1700, such as during start-up, may be stored in memory 1708. Memory 1708 may also include (e.g., stored on one or more machine-readable media) instructions (e.g., software) 1720 embodying any one or more of the aspects and/or methodologies of the present disclosure. In another example, memory 1708 may further include any number of program modules including, but not limited to, an operating system, one or more application programs, other program modules, program data, and any combinations thereof.

Computer system 1700 may also include a storage device 1724. Examples of a storage device (e.g., storage device 1724) include, but are not limited to, a hard disk drive, a magnetic disk drive, an optical disc drive in combination with an optical medium, a solid-state memory device, and any combinations thereof. Storage device 1724 may be connected to bus 1712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1724 (or one or more components thereof) may be removably interfaced with computer system 1700 (e.g., via an external port connector (not shown)). Particularly, storage device 1724 and an associated machine-readable medium 1728 may provide nonvolatile and/or volatile storage of machine-readable instructions, data structures, program modules, and/or other data for computer system 1700. In one example, software 1720 may reside, completely or partially, within machine-readable medium 1728. In another example, software 1720 may reside, completely or partially, within processor 1704.

Computer system 1700 may also include an input device 1732. In one example, a user of computer system 1700 may enter commands and/or other information into computer system 1700 via input device 1732. Examples of an input device 1732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1732 may be interfaced to bus 1712 via any of a variety of interfaces (not shown) including, but not limited to, a serial interface, a parallel interface, a game port, a USB interface, a FIREWIRE interface, a direct interface to bus 1712, and any combinations thereof. Input device 1732 may include a touch screen interface that may be a part of or separate from display 1736, discussed further below. Input device 1732 may be utilized as a user selection device for selecting one or more graphical representations in a graphical interface as described above.

A user may also input commands and/or other information to computer system 1700 via storage device 1724 (e.g., a removable disk drive, a flash drive, etc.) and/or network interface device 1740. A network interface device, such as network interface device 1740, may be utilized for connecting computer system 1700 to one or more of a variety of networks, such as network 1744, and one or more remote devices 1748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1744, may employ a wired and/or a wireless mode of communication. In general, any network topology may be used. Information (e.g., data, software 1720, etc.) may be communicated to and/or from computer system 1700 via network interface device 1740.

Computer system 1700 may further include a video display adapter 1752 for communicating a displayable image to a display device, such as display device 1736. Examples of a display device include, but are not limited to, a liquid crystal display (LCD), a cathode ray tube (CRT), a plasma display, a light emitting diode (LED) display, and any combinations thereof. Display adapter 1752 and display device 1736 may be utilized in combination with processor 1704 to provide graphical representations of aspects of the present disclosure. In addition to a display device, computer system 1700 may include one or more other peripheral output devices including, but not limited to, an audio speaker, a printer, and any combinations thereof. Such peripheral output devices may be connected to bus 1712 via a peripheral interface 1756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for using artificial intelligence to analyze user activity data, the system comprising:
    at least a server, wherein the at least a server is designed and configured to:
    receive training data, wherein receiving training data further comprises receiving a training set including a plurality of first data entries, each first data entry of the plurality of first data entries including at least an element of physiological state data and at least a correlated compatible label;
    receive from a user, at least a biological extraction and at least a user activity datum, said biological extraction including data related to a physiological state of a user;
    generate a diagnostic output as a function of the physiological state of the user, wherein the diagnostic output comprises a condition of the user associated with an ingredient having an adverse effect on the condition of the user;
    retrieve from a fingerprint database, at least a datum of user fingerprint information;
    classify the at least a user activity datum as a function of the at least a datum of user fingerprint information wherein classifying the at least a user activity datum comprises identifying a category of the at least a user activity datum;
    select at least a compatible element as a function of the training data, the category of at least a user activity datum, and the condition of the user;
    rank the selected at least a compatible element within a plurality of compatible elements as a function of a respective presence of the ingredient having an adverse effect on the condition of the user within each of the plurality of compatible elements; and
    transmit the ranked plurality of compatible elements to a user client device.

2. The system of claim 1, wherein the at least a server further comprises:
    a parsing module configured to extract at least an element from the at least a user activity datum wherein the at least an element further comprises at least a compatible element neutralizer; and
    retrieve at least a datum of user fingerprint information as a function of the at least an element.

3. The system of claim 1, wherein the at least a server is further configured to receive at least a user activity datum and retrieve from a behavior database at least a datum of user behavior data.

4. The system of claim 1, wherein the at least a server is further configured to classify the at least a user activity datum by matching the at least a datum of user fingerprint information to at least a datum of previous user activity.

5. The system of claim 1, wherein the at least a server is further configured to classify the at least a user activity datum as a function of receiving at least a datum of modified user activity.

6. The system of claim 1, wherein the at least a server is further configured to select at least a compatible element using a machine-learning algorithm and the training data.

7. The system of claim 1, wherein the at least a server is further configured to select at least a compatible element by:
    retrieving at least a compatible element similarity index value from a database; and
    selecting at least a compatible element as a function of the compatible element similarity index value.

8. The system of claim 1, wherein the at least a server is further configured to store the at least a user activity datum in the fingerprint database.

9. A method of using artificial intelligence to analyze user activity data, the method comprising:
    receiving by at least a server training data, wherein receiving training data further comprises receiving a training set including a plurality of first data entries, each first data entry of the plurality of first data entries including at least an element of physiological state data and at least a correlated compatible label;
    receiving by the at least a server at least a biological extraction and at least a user activity datum from a user, said biological extraction including data related to a physiological state of the user;
    generating a diagnostic output as a function of the training data and the physiological state of the user;
    retrieving by the at least a server at least a datum of user fingerprint information from a fingerprint database;
    classifying by the at least a server the at least a user activity datum as a function of the at least a datum of user fingerprint information;
    selecting by the at least a server at least a compatible element as a function of the at least a user activity datum and the diagnostic output; and transmitting by the at least a server the at least a compatible element to a user client device.

10. The method of claim 9, wherein receiving at least a user activity datum further comprises:
   extracting at least an element from the at least a user activity datum wherein the at least an element further comprises at least a compatible element neutralizer; and
   retrieving at least a datum of user fingerprint information as a function of the at least an element.

11. The method of claim 9, wherein receiving at least a user activity datum further comprises retrieving from a behavior database at least a datum of user behavior data.

12. The method of claim 9, wherein classifying the at least a user activity datum further comprises matching the at least a datum of user fingerprint information to at least a datum of previous user activity.

13. The method of claim 9, wherein classifying the at least a user activity datum further comprises classifying the at least a user activity datum as a function of receiving at least a datum of modified user activity.

14. The method of claim 9, wherein selecting at least a compatible element further comprises using a machine-learning algorithm and the training data.

15. The method of claim 9, wherein selecting at least a compatible element further comprises:
   retrieving at least a compatible element similarity index value from a database; and
   selecting at least a compatible element as a function of the compatible element similarity index value.

16. The method of claim 9 further comprising storing the at least a user activity datum in the fingerprint database.

* * * * *